(12) United States Patent
Kim et al.

(10) Patent No.: US 9,075,064 B2
(45) Date of Patent: Jul. 7, 2015

(54) METHOD FOR DECREASING RADIORESISTANCE AND GROWTH, METASTASIS AND INFILTRATION OF CANCER CELLS THROUGH REGULATING EXPRESSION OR ACTIVITY OF TM4SF4 IN NON-SMALL CELL LUNG CANCER

(75) Inventors: In-Gyu Kim, Daejeon (KR); Soo Im Choi, Daejeon (KR); Byung-Chul Shin, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 14/347,506

(22) PCT Filed: Oct. 21, 2011

(86) PCT No.: PCT/KR2011/007900
§ 371 (c)(1),
(2), (4) Date: Mar. 26, 2014

(87) PCT Pub. No.: WO2013/047941
PCT Pub. Date: Apr. 4, 2013

(65) Prior Publication Data
US 2014/0234326 A1 Aug. 21, 2014

(30) Foreign Application Priority Data
Sep. 26, 2011 (KR) .................. 10-2011-0096918

(51) Int. Cl.
| | |
|---|---|
| A61K 39/395 | (2006.01) |
| G01N 33/574 | (2006.01) |
| A61K 31/7105 | (2006.01) |
| A61K 31/713 | (2006.01) |
| C12N 15/113 | (2010.01) |
| C07K 14/705 | (2006.01) |
| C07K 16/30 | (2006.01) |
| C12Q 1/68 | (2006.01) |
| G01N 33/50 | (2006.01) |
| C07K 16/28 | (2006.01) |
| A61K 48/00 | (2006.01) |

(52) U.S. Cl.
CPC .......... *G01N 33/57423* (2013.01); *A61K 48/00* (2013.01); *A61K 31/7105* (2013.01); *A61K 31/713* (2013.01); *C12N 15/1138* (2013.01); *C12N 2310/14* (2013.01); *C07K 14/705* (2013.01); *C07K 16/3023* (2013.01); *C12Q 1/6886* (2013.01); *G01N 33/5011* (2013.01); *C07K 16/28* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2002/0115057 A1* | 8/2002 | Young | 435/4 |
| 2008/0193454 A1* | 8/2008 | Tureci et al. | 424/138.1 |
| 2010/0081638 A1* | 4/2010 | Lee et al. | 514/169 |
| 2011/0177098 A1* | 7/2011 | Sussel et al. | 424/173.1 |

FOREIGN PATENT DOCUMENTS

| | | |
|---|---|---|
| JP | 2008/283945 | 11/2008 |
| KR | 2008-0052391 | 6/2008 |
| KR | 10-0934706 | 12/2009 |

OTHER PUBLICATIONS

Dandrea et al (Free Radical Biology & Medicine, 36:881-896).*
Franklin et al (11th World Conference on Lung Cancer, Jul. 3-6, 2005, Barcelona, Spain, abstract P-245).*
Nakamura et al (Oncogene, 2006, 25:4245-4255).*
Qiu et al., "Overexpression of the gene for transmembrane 4 superfamily member 4 accelerates liver damage in rats treated with $CCl_4$," *Journal of Hepatology*, vol. 46, pp. 266-275, 2007.

* cited by examiner

*Primary Examiner* — Laura B Goddard
(74) *Attorney, Agent, or Firm* — Klarquist Sparkman, LLP

(57) ABSTRACT

The present invention relates to a pharmaceutical composition or an anticancer agent for preventing and treating non-small cell lung cancer, containing a substance for regulating the expression or activity of transmembrane 4 L six family member 4 (TM4SF4). More specifically, the present invention relates to a use of a substance for regulating the expression or activity of TM4SF4 as an anticancer drug or an anticancer agent with respect to non-small cell lung cancer, wherein it was ascertained that it is possible to decrease the growth, metastasis, and infiltration of adenocarcinoma cells and radioresistance by decreasing the expression of TM4SF4 in adenocarcinoma among non-small cell lung cancers and to decrease the growth, metastasis, and infiltration of the cells and radioresistance by increasing the expression of TM4SF4 in other non-small cell lung cancers except adenocarcinoma.

4 Claims, 16 Drawing Sheets

Fig. 8
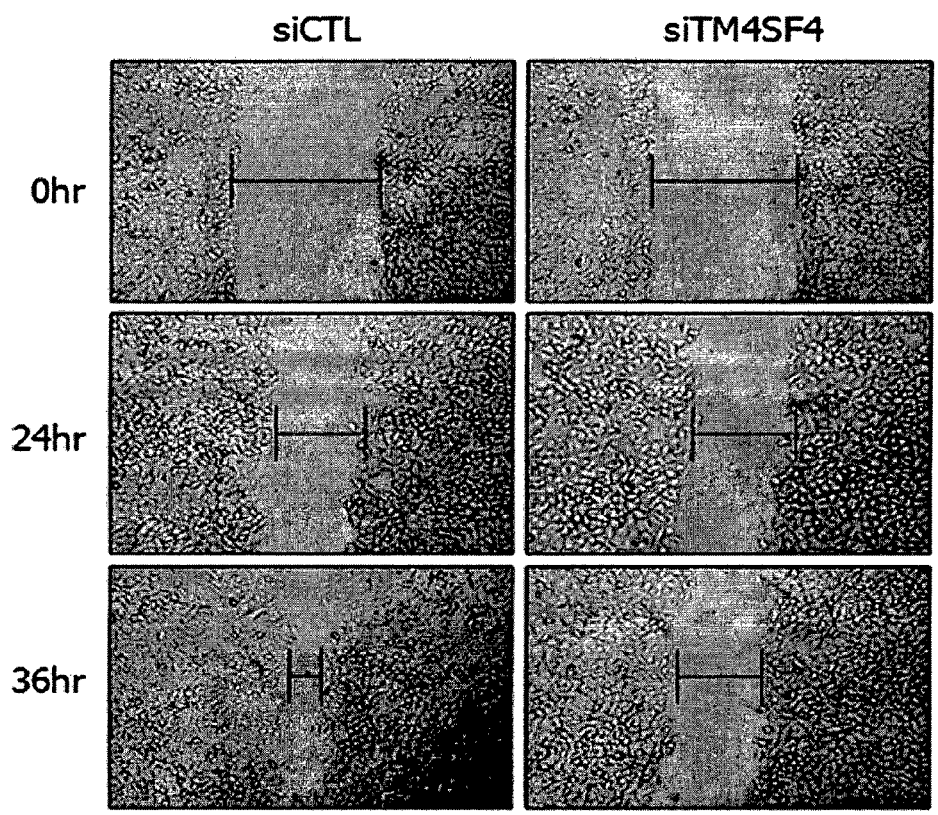
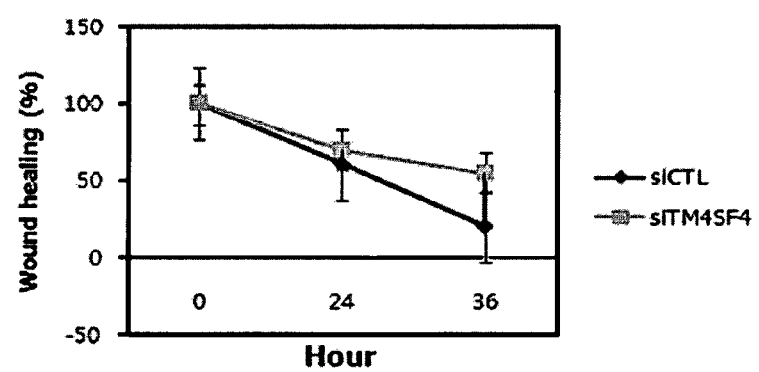

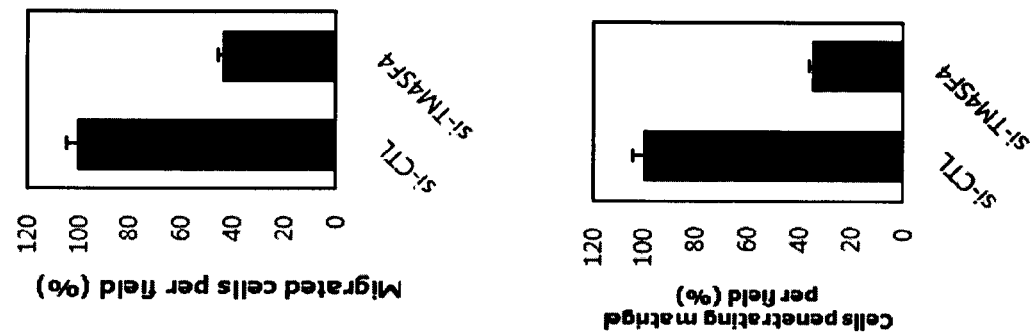
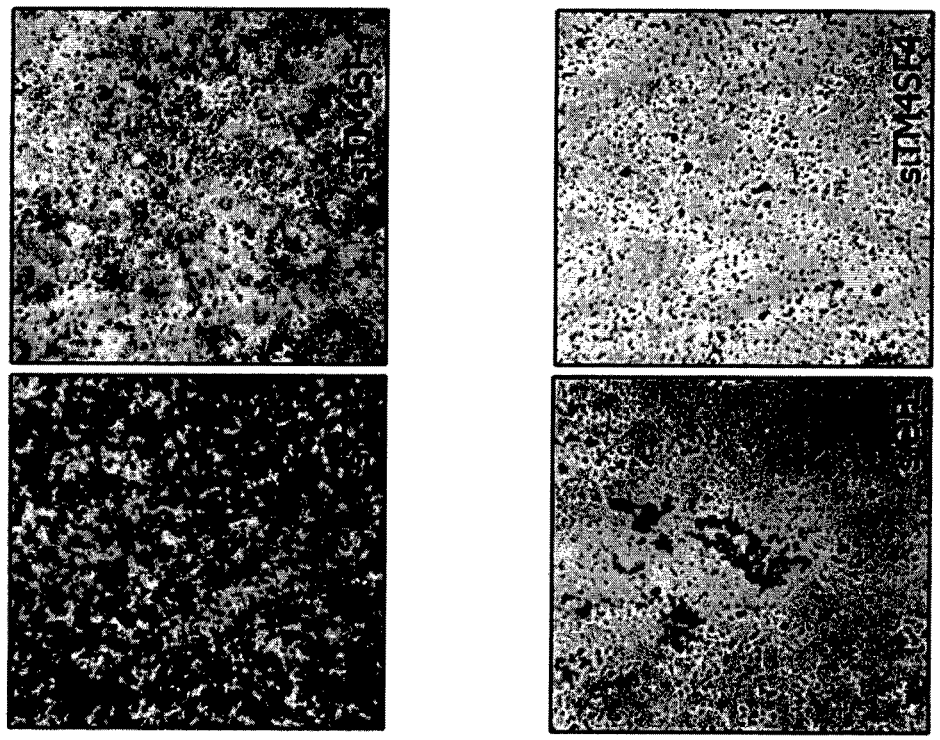
Fig. 9
Migration
Invasion

Fig. 10
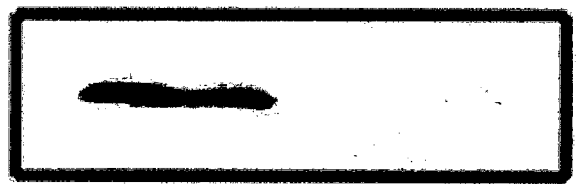
MMP2
MMP7
MMP9
β-actin

Fig. 13
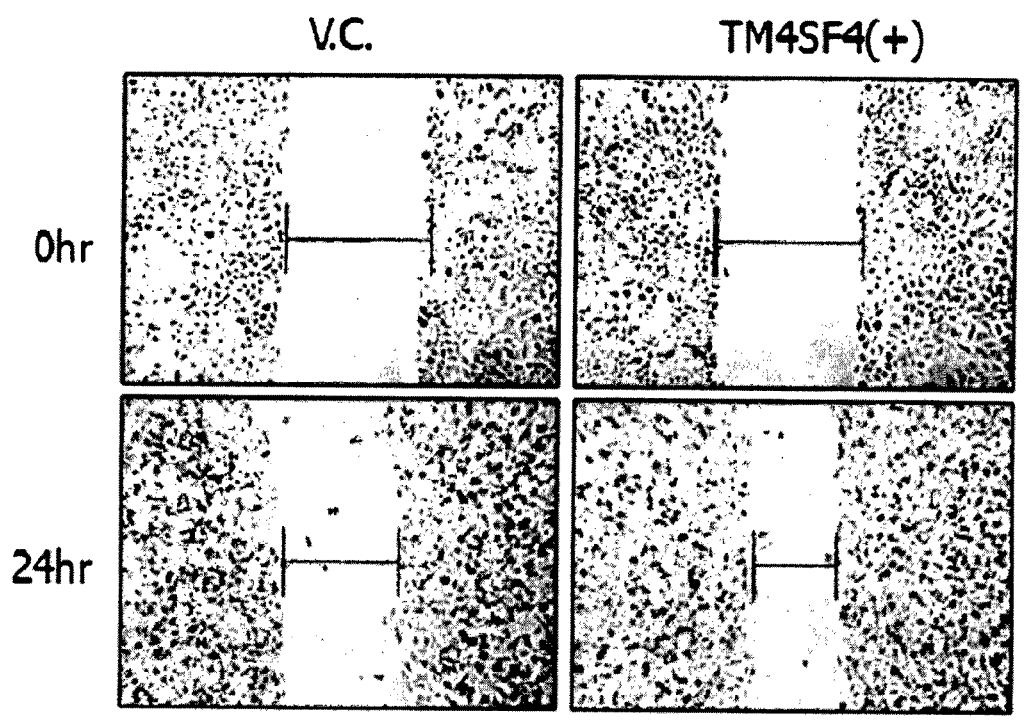
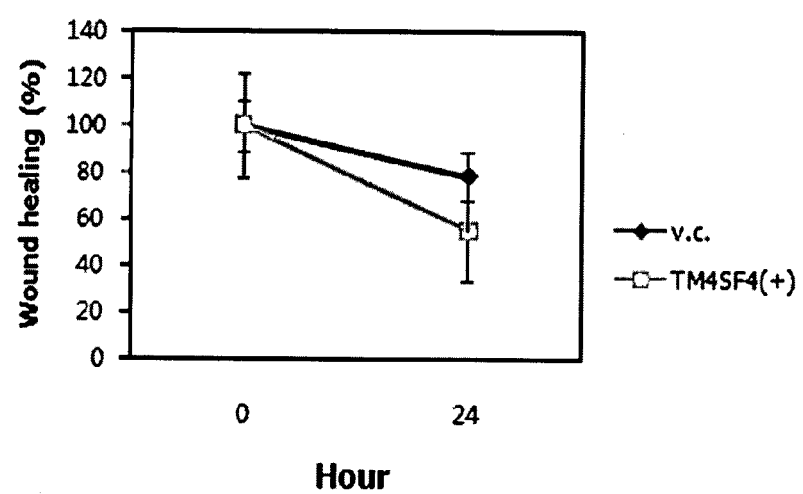

Fig. 15
 MMP2
 MMP7
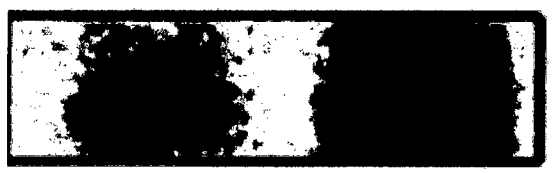 MMP9
 β-actin

Fig. 16
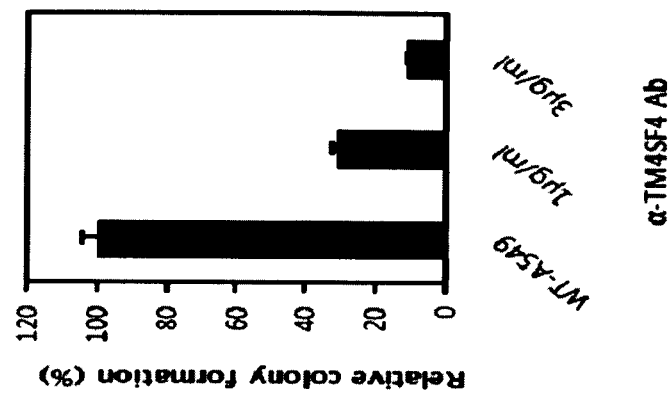
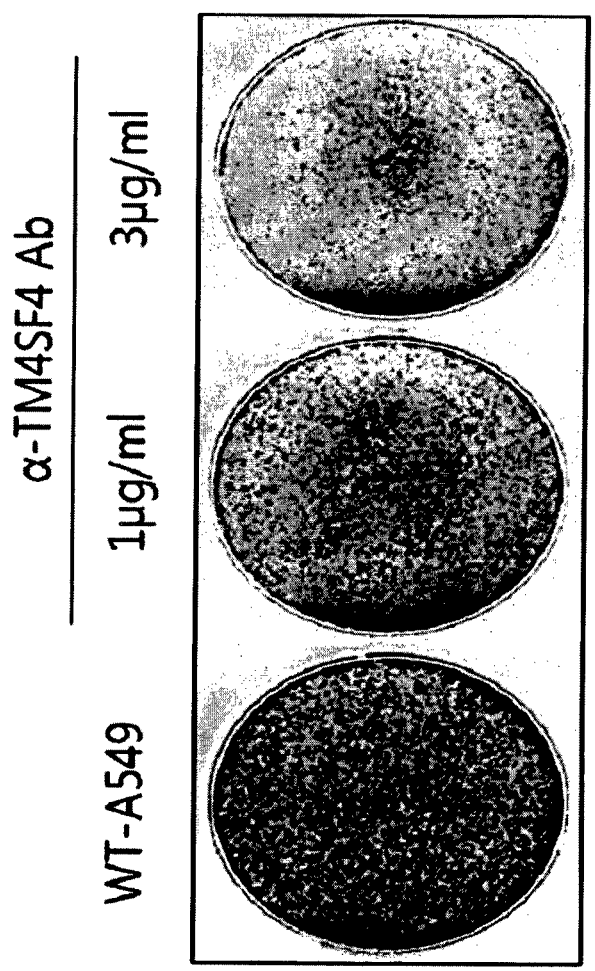

SEQUENCE LISTING

<160> NUMBER OF SEQ ID NOS: 9

<210> SEQ ID NO 1
<211> LENGTH: 202
<212> TYPE: PRT
<213> ORGANISM: Homo sapiens

<400> SEQUENCE: 1

Met Cys Thr Gly Gly Cys Ala Arg Cys Leu Gly Gly Thr Leu Ile Pro
1               5                   10                  15

Leu Ala Phe Phe Gly Phe Leu Ala Asn Ile Leu Leu Phe Phe Pro Gly
                20                  25                  30

Gly Lys Val Ile Asp Asp Asn Asp His Leu Ser Gln Glu Ile Trp Phe
            35                  40                  45

Phe Gly Gly Ile Leu Gly Ser Gly Val Leu Met Ile Phe Pro Ala Leu
        50                  55                  60

Val Phe Leu Gly Leu Lys Asn Asn Asp Cys Cys Gly Cys Cys Gly Asn
65                  70                  75                  80

Glu Gly Cys Gly Lys Arg Phe Ala Met Phe Thr Ser Thr Ile Phe Ala
                85                  90                  95

Val Val Gly Phe Leu Gly Ala Gly Tyr Ser Phe Ile Ile Ser Ala Ile
            100                 105                 110

Ser Ile Asn Lys Gly Pro Lys Cys Leu Met Ala Asn Ser Thr Trp Gly
        115                 120                 125

Tyr Pro Phe His Asp Gly Asp Tyr Leu Asn Asp Glu Ala Leu Trp Asn
    130                 135                 140

Lys Cys Arg Glu Pro Leu Asn Val Val Pro Trp Asn Leu Thr Leu Phe
145                 150                 155                 160

Ser Ile Leu Leu Val Val Gly Gly Ile Gln Met Val Leu Cys Ala Ile
                165                 170                 175

Gln Val Val Asn Gly Leu Leu Gly Thr Leu Cys Gly Asp Cys Gln Cys
            180                 185                 190

Cys Gly Cys Cys Gly Gly Asp Gly Pro Val
        195                 200

<210> SEQ ID NO 2
<211> LENGTH: 609
<212> TYPE: DNA
<213> ORGANISM: Homo sapiens

<400> SEQUENCE: 2
atgtgcactg ggggctgtgc cagatgcctg gggggaccc tcattcccct tgcttttttt        60
ggcttcctgg ctaacatcct gttatttttt cctggaggaa aagtgataga tgacaacgac       120
cacctttccc aagagatctg gttttcgga ggaatattag gaagcggtgt cttgatgatc       180

```
ttccctgcgc tggtgttctt gggcctgaag aacaatgact gctgtgggtg ctgcggcaac    240
gagggctgtg ggaagcgatt tgcgatgttc acctccacga tatttgctgt ggttggattc    300
ttgggagctg atactcgtt tatcatctca gccatttcaa tcaacaaggg tcctaaatgc     360
ctcatggcca atagtacatg gggctacccc ttccacgacg gggattatct caatgatgag    420
gccttatgga acaagtgccg agagcctctc aatgtggttc cctggaatct gaccctcttc    480
tccatcctgc tggtcgtagg aggaatccag atggttctct cgccatcca ggtggtcaat     540 ggcctcctgg ggaccctctg tggggactgc cagtgttgtg gctgctgtgg gggagatgga    600
cccgtttaa                                                            609

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 3
ccacgaattc atgtgcactg ggggc                                           25

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 4
tcctcgagtt aaacgggtcc atctccc                                         27

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 5
catcctcacc ctgaagtacc c                                               21

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
agcctggata gcaacgtaca tg                                              22

<210> SEQ ID NO 7
<211> LENGTH: 25
<212> TYPE: RNA
<213> ORGANISM: Artificial Sequence
<220> FEATURE:
<223> OTHER INFORMATION: siRNA

<400> SEQUENCE: 7
gccucucaau gugguucccu ggaau                                           25

<210> SEQ ID NO 8
<211> LENGTH: 25
```

```
<212> TYPE: RNA
<213> ORGANISM: Artificial Sequence
<220> FEATURE:
<223> OTHER INFORMATION: siRNA

<400> SEQUENCE: 8
auuccaggga accacauuga gaggc                                              25

<210> SEQ ID NO 9
<211> LENGTH: 25
<212> TYPE: DNA
<213> ORGANISM: Homo sapiens

<400> SEQUENCE: 9
gcctctcaat gtggttccct ggaat                                              25
```

METHOD FOR DECREASING RADIORESISTANCE AND GROWTH, METASTASIS AND INFILTRATION OF CANCER CELLS THROUGH REGULATING EXPRESSION OR ACTIVITY OF TM4SF4 IN NON-SMALL CELL LUNG CANCER

CROSS REFERENCE TO RELATED APPLICATIONS

This is the §371 U.S. National Stage of International Application No. PCT/KR2011/007900, filed Oct. 21, 2011, which in turn claims the benefit of KR Application No. 10-2011-0096918, filed Sep. 26, 2011, which is incorporated by reference herein in its entirety.

SEQUENCE LISTING

The Sequence Listing is submitted as an ASCII text file in the form of the file named Sequence_Listing.txt, which was created on Mar. 21, 2014, and is 4,555 bytes, which is incorporated by reference herein.

BACKGROUND OF THE INVENTION

1. Field of the Invention

The present invention relates to an anticancer drug or an anticancer agent for preventing and treating non-small cell lung cancer, comprising a substance for regulating the expression or activity of TM4SF4 (transmembrane 4 L six family member 4) as an active ingredient.

2. Description of the Related Art

Lung cancer is the second most frequent cancer among both men and women, which takes 15% of all cancers. According to the recent report made by American Cancer Society in 2011, at least 220,000 cases of cancer are diagnosed as lung cancer annually, among which approximately 70% of patients die which takes 27% of total death of cancer. Particularly, non-small cell lung cancer is a kind of carcinoma that generally includes all epithelial lung cancers except small cell lung cancer. Non-small cell lung cancer takes about 85%~90% of total lung cancer. Non-small cell lung cancer is comparatively less sensitive to chemotherapy than small cell lung cancer. Stages of this cancer are divided by TNM classification which considers the size of tumor, diffusion to regional lymph node, and metastasis, etc. In the treatment of non-small cell lung cancer, the early stage of non-metastatic non-small cell lung cancer demonstrates very low sensitivity to chemotherapy and radiotherapy, so that ancillary chemotherapy using cisplatin comprising platinum is generally co-treated with surgical operation. However, when the cancer progresses to metastatic non-small cell lung cancer passing through the early stage, various chemotherapy and radiotherapy are used. Symptoms of non-small cell lung cancer are constant cough, chest pain, weight loss, nail damage, arthrodynia, shortness of breath, etc. In general, non-small cell lung cancer progresses slowly, so almost no symptoms are observed in its early stage. Therefore, it is as difficult to pick up this non-small cell lung cancer as to treat it. In most cases, once it transfers to the whole body, for example bone, liver, small intestines, and brain, it is then diagnosed. In spite of high incidence rate and high death rate, any efficient drug or treatment method to overcome non-small cell lung cancer has not been developed, yet, emphasizing the necessity of it. Non-small cell lung cancer is divided into a few sub-groups according to the size, the shape, and the chemical composition of cancer cell, which are represented by adenocarcinoma, squamouse cell carcinoma, and large cell carcinoma. Adenocarcinoma is a kind of lung cancer that is most frequently observed which takes at least 40% of total lung cancer. Adenocarcinoma is usually developed in outer region of the lung and progresses more slowly than other lung cancers. However, adenocarcinoma shows high tendency of metastasis in the early stage and high radioresistance. Squamouse cell carcinoma is a kind of non-small cell lung cancer that takes 25~30% of total lung cancer. It starts in early version of cells forming airway. This cancer occurs highly in smokers. Large cell carcinoma can be developed in any region of the lung and takes 10~15% of total lung cancer. Progression rate of this cancer is as fast as that of small cell lung cancer, which makes the treatment still difficult.

Cancer development starts from abnormal cell growth. When any gene, for example the gene playing a certain role in cell cycle or the gene that is responsible for DNA repair mechanism for auto-elimination of mutation, is mutated, tumor suppressor gene is inactivated or oncogene is activated, resulting in the abnormal cell growth or abnormal cell proliferation. For instance, non-small cell lung cancer starts with the mutation of EGFR (epidermal growth factor receptor) and then keeps being activated without its ligand EGF (epidermal growth factor), which is abnormal proliferation or growth (non-patent reference 1). PI3K (phosphatidylinositol 3-kinases)-Akt (protein kinase B) pathway is an important intracellular signal pathway for cell proliferation and migration. In cancer cells, the PI3K-Akt signal pathway is always activated, unlike in normal cells. The most characteristic factor of cancer cell is the over-expression of MMP (matrix metalloprotease). MMP is a protease that degrades extracellular matrix whose activity is essential for cell migration, intravasion, extravasion, angiogenesis, and metastasis. MMP is generally expressed only when necessary for tissue remodeling or wound healing. However in cancer cells, MMP is over-expressed to mediate cancer cell migration, cancer cell growth, and metastasis (non-patent reference 2). Unlike normal cells therefore, cancer cells are excessively grown to be transferred to other organs, which means cancer cells spread to the whole body to destroy normal tissues unless treated.

TM4SF4 (transmembrane 4 L six family member 4) is a kind of cell membrane protein called tetraspanin, which is a member of transmembrane 4 superfamily of L6 (non-patent reference 3). Cell membrane protein belonging to tetraspanin superfamily is involved in many biological systems relating to diseases including cancer, suggesting that it is involved in a wide spectrum of various processes occurring in cells, according to a previous report. Most previous studies stated that the expression of tetraspanin is involved in the regulation of cancer development marker and is at least believed to be involved in the malignancy of cancer cells (non-patent reference 4). Transmembrane 4 L6 superfamily includes L6, L6D, TM4SF4, and TM4SF5. The whole structures of them are similar and the difference is only made by C-terminal. TM4SF5 is closely related to tumorigenesis and metastasis (non-patent reference 5-6). It has also been reported that TM4SF4 is involved in rat pancreas differentiation and hepatocyte regeneration in the developmental stage (non-patent reference 7-8). TM4SF4 has also been reported to belong to the candidate gene group that shows low expression in normal cells but high expression in adenocarcinoma cells (non-patent reference 9). Nevertheless, there is no report yet in relation to the accurate function of TM4SF4. In particular, there are no studies so far conducted with human cells and cancer cells to disclose the specific function of TM4SF4.

Thus, the present inventors tried to disclose the function of TM4SF4 in cancer cells. As a result, the inventors confirmed that the expression of TM4SF4 varies from the type of non-small cell lung cancer and the control of TM4SF4 expression might affect radioresistance, cell growth, metastasis, and infiltration of non-small cell lung cancer cells. Particularly, adenocarcinoma cell lines (A549, Calu-3) showed higher TM4SF4 expression, compared with other cell lines of non-small cell lung cancer. When the expression or activity of TM4SF4 was suppressed by using TM4SF4 antibody or siRNA, not only cancer progress, cell growth, metastasis, and infiltration, but also radioresistance was all reduced. In the meantime, in other non-small cell lung cancer cell lines except adenocarcinoma showing comparatively low TM4SF4 expression, when the expression of TM4SF4 was increased by using TM4SF4 expression vector, cell growth and radioresistance were decreased. The present inventors further confirmed that the regulation of TM4SF4 expression and activation brought the above effect by regulating the activity of IGF1R/PI3K-Akt/NK-κB and the expression of MMP in cancer cells. As a result, the present inventor completed this invention by confirming that the pharmaceutical composition that is able to reduce the expression of TM4SF4 was effective in preventing and treating adenocarcinoma among non-small cell lung cancers, and the pharmaceutical composition that is able to increase the expression of TM4SF4 was effective in preventing and treating non-small cell lung cancers except adenocarcinoma and was more effective when co-treated with radiotherapy.

PRIOR ART REFERENCE

Non-Patent Reference (Non-Patent Reference 1) Fresno Vara J A. et al., Cancer Treat Rev. 2004 April; 30(2):193-204.
(Non-Patent Reference 2) Joyce E. Rundhaug., Clin Cancer Res 2003; 9(2):551-4.
(Non-Patent Reference 3) Wright M D et al., Protein Sci 2000; 9(8):1594-1600.
(Non-Patent Reference 4) Zevian S et al., J. Biol. Chem. 2001; 286(9):7496-7506.
(Non-Patent Reference 5) Lee S A et al., J. Clin. Invest. 2008; 118(4):1354-66.
(Non-Patent Reference 6) Lee S A et al., Blood. 2009; 113 (8):1845-55.
(Non-Patent Reference 7) Liu Z et al., Biochim. Biophys. Acta 2001; 1518(1-2):183-9.
(Non-Patent Reference 8) Anderson K R et al., Development 2011; 138(15):3213-24.
(Non-Patent Reference 9) Nakamura N et al., Oncogene 2006 28; 4245-4255.

SUMMARY OF THE INVENTION

It is an object of the present invention to provide an anticancer drug or an anticancer agent for preventing and treating non-small cell lung cancer that is effective in suppressing non-small cell lung cancer cell growth, metastasis, and infiltration as well as in increasing radiosensitivity by using a substance for regulating the expression or activity of TM4SF4 (transmembrane 4 L six family member 4).

To achieve the above object, the present invention provides a pharmaceutical composition for preventing and treating adenocarcinoma among non-small cell lung cancers, comprising an inhibitor of the expression or activity of TM4SF4 (transmembrane 4 L six family member 4) as an active ingredient.

The present invention also provides an anticancer agent for adenocarcinoma among non-small cell lung cancers comprising an inhibitor of the expression or activity of TM4SF4 as an active ingredient.

The present invention further provides a pharmaceutical composition for preventing and treating non-small cell lung cancers except adenocarcinoma comprising an expression vector harboring a gene encoding TM4SF4 protein as an active ingredient.

The present invention also provides an anticancer agent for non-small cell lung cancers except adenocarcinoma comprising an expression vector harboring a gene encoding TM4SF4 protein as an active ingredient.

The present invention also provides a composition for increasing radiosensitivity of adenocarcinoma cells among non-small cell lung cancer cells comprising an inhibitor of the expression or activity of TM4SF4 as an active ingredient.

The present invention also provides a composition for increasing radiosensitivity of non-small cell lung cancer cells except adenocarcinoma cells comprising an expression vector harboring a gene encoding TM4SF4 protein as an active ingredient.

The present invention also provides a method for increasing radiosensitivity of adenocarcinoma cells among non-small cell lung cancer cells comprising the step of administering an inhibitor of the expression or activity of TM4SF4 to adenocarcinoma cells among non-small cell lung cancer cells.

The present invention also provides a method for increasing radiosensitivity of non-small cell lung cancer cells except adenocarcinoma cells comprising the step of administering a vector containing TM4SF4 gene to non-small cell lung cancer cells except adenocarcinoma cells.

The present invention also provides a method for screening an anticancer drug or an enhancer candidate to increase radiosensitivity of adenocarcinoma cells among non-small cell lung cancer cells comprising the following steps:
1) treating test materials to the cell line expressing TM4SF4 protein;
2) measuring the expression or activity of TM4SF4 protein in the above cell line; and
3) selecting the test material demonstrating lower expression or activity of TM4SF4 protein than that of the control non-treated with the test material.

The present invention also provides a method for screening an anticancer drug or an enhancer candidate to increase radiosensitivity of non-small cell lung cancer cells except adenocarcinoma cells comprising the following steps:
1) treating test materials to the cell line expressing TM4SF4 protein TM4SF4;
2) measuring the expression or activity of TM4SF4 protein in the above cell line; and
3) selecting the test material demonstrating higher expression or activity of TM4SF4 protein than that of the control non-treated with the test material.

The present invention also provides a method for treating adenocarcinoma among non-small cell lung cancers, comprising the step of administering a pharmaceutically effective dose of an inhibitor of TM4SF4 expression or activity to a subject having adenocarcinoma.

The present invention also provides a method for preventing adenocarcinoma among non-small cell lung cancers, comprising the step of administering a pharmaceutically effective dose of an inhibitor of TM4SF4 expression or activity to a subject.

The present invention also provides a method for treating non-small cell lung cancer except adenocarcinoma comprising the step of administering a pharmaceutically effective dose of an expression vector harboring a gene encoding TM4SF4 protein to a subject having non-small cell lung cancer except adenocarcinoma.

The present invention also provides a method for preventing non-small cell lung cancer except adenocarcinoma comprising the step of administering a pharmaceutically effective dose of an expression vector harboring a gene encoding TM4SF4 protein to a subject.

The present invention also provides a use of the inhibitor of TM4SF4 expression or activity as a pharmaceutical composition for the prevention and treatment of adenocarcinoma among non-small cell lung cancer.

The present invention also provides a use of the inhibitor of TM4SF4 expression or activity as an anticancer agent for adenocarcinoma among non-small cell lung cancer.

The present invention also provides a use of the expression vector containing the gene encoding TM4SF4 protein as a pharmaceutical composition for the prevention and treatment of non-small cell lung cancer except adenocarcinoma.

The present invention also provides a use of the expression vector containing the gene encoding TM4SF4 protein as an anticancer agent for non-small cell lung cancer except adenocarcinoma.

The present invention also provides a use of the inhibitor of TM4SF4 expression or activity as an enhancer of radiosensitivity of adenocarcinoma cells among non-small cell lung cancer cells.

In addition, the present invention also provides a use of the expression vector containing the gene encoding TM4SF4 as an enhancer of radiosensitivity of non-small cell lung cancer cells except adenocarcinoma cells.

Advantageous Effect

As explained hereinbefore, the present invention proved that cancer cell growth, metastasis, infiltration, and radioresistance were decreased by regulating the expression and activity of TM4SF4 (transmembrane 4 L six family member 4) in non-small cell lung cancer cell lines. Particularly, when the expression or activity of TM4SF4 was suppressed in adenocarcinoma cells among non-small cell lung cancer cells, cancer cell growth, metastasis, and infiltration were all reduced but radiosensitivity was significantly increased. On the other hand, when the expression of TM4SF4 was increased in other non-small cell lung cancer cells except adenocarcinoma cells, cell growth and radioresistance were decreased. Therefore, a pharmaceutical composition regulating the expression or activity of TM4SF4 can be effectively used for the prevention and treatment of cancer.

BRIEF DESCRIPTION OF THE DRAWINGS

The application of the preferred embodiments of the present invention is best understood with reference to the accompanying drawings, wherein:

FIG. 8 is a diagram illustrating the result of observation on time-dependent migration in both A549 cells with suppressed TM4SF4 and in the control A549 cells via wound healing method.

FIG. 9 is a diagram illustrating the comparison of migration and infiltration between the A549 cells with suppressed TM4SF4 and the control A549 cells.

FIG. 10 is a diagram illustrating the result of Western blotting performed to investigate the correlation between the suppression of TM4SF4 and MMP-2,7,9 in A549 cells.

FIG. 13 is a diagram illustrating the result of observation of wound healing performed to investigate cell migration induced by TM4SF4 over-expression in A549 cells.

FIG. 15 is a diagram illustrating the result of Western blotting performed to investigate the correlation between the over-expression of TM4SF4 and MMP-2,7,9 in A549 cells.

FIG. 16 is a diagram illustrating the result of colony formation analysis performed to investigate TM4SF4 antibody dose-dependent cell proliferation in A549 cells with over-expressed TM4SF4.

DESCRIPTION OF THE PREFERRED EMBODIMENTS

Figure 1:
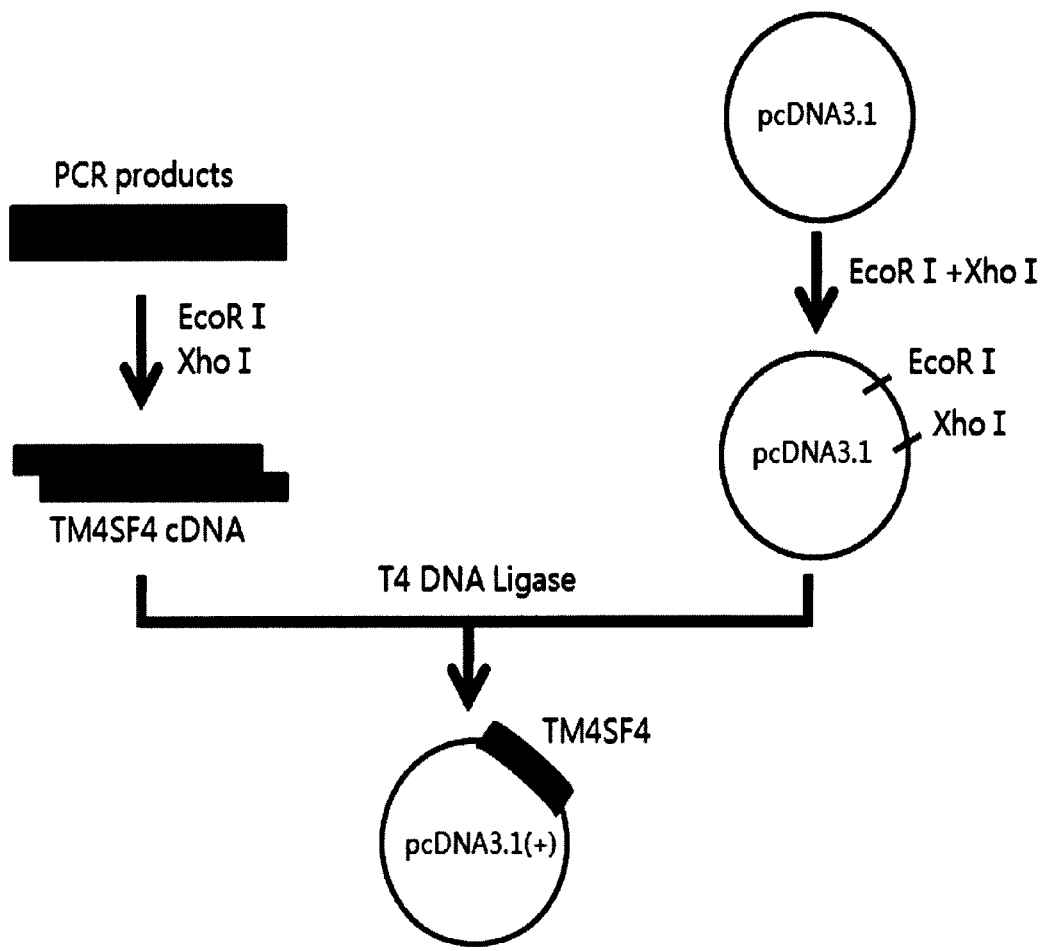
FIG. 1 is a diagram illustrating the process of cloning of the expression vector TM4SF4/pcDNA3.1 in various lung cancer cell lines in order to induce the over-expression of TM4SF4 via transfection.

Hereinafter, the present invention is described in detail.

The present invention provides a pharmaceutical composition for preventing and treating adenocarcinoma among non-small cell lung cancers, comprising an inhibitor of the expression or activity of TM4SF4 (transmembrane 4 L six family member 4) as an active ingredient.

The said TM4SF4 protein is composed of the amino acid sequence represented by SEQ. ID. NO: 1, but not always limited thereto. The sequence can include such amino acid sequence that has deletion, addition, or substitution with some of amino acids in the said amino acid sequence, and those sequences having preferably at least 80%, more preferably at least 90% homology can also be included.

The effective inhibitor of TM4SF4 expression herein is antisense nucleotide or small interfering RNA (siRNA) complementarily binding to mRNA, but not always limited thereto.

The inhibitor of TM4SF4 expression herein does suppress the expression of TM4SF4 as a normal active protein by intervening transcription of TM4SF4 gene, post-transcription, translation, or post-translational process. More precisely, the said inhibitor is preferably antisense nucleotide or small interfering RNA (siRNA) complementarily binding to TM4SF4 mRNA, but not always limited thereto. The antisense nucleotide herein inhibits the protein expression by binding to DNA, immature-mRNA, or mature mRNA, according to the definition by Watson-Crick base pair. Target sequence specific antisense nucleotide is characterized by multi-functions. Antisense nucleotide is a long chain monomer, so that it can be easily synthesized with target RNA sequence. The said siRNA is 15~30 mer or more preferably 20~25 mer selected from the nucleotide sequence of mRNA of the gene encoding human TM4SF4 protein (SEQ. ID. NO: 2), but not always limited thereto and can be any antisense sequence capable of binding complementarily to the sense sequence. At this time, the sense sequence is not limited to a specific one, and can be composed of 19 nucleotides, but not always limited thereto, either. In many recent researches, the usability of antisense nucleotide, particularly siRNA targeting mRNA, has been proved as a biochemical tool to study target protein (Rothenberg et al., *J. Natl. Cancer Inst.*, 81:1539-1544, 1999). Great advance has been made in the field of oligonucleotide chemistry and synthesis of nucleotide demonstrating improved cell adhesion, target binding affinity, and nuclease resistance, etc. Accordingly, antisense nucleotide can be considered as a novel inhibitor.

The effective inhibitor of TM4SF4 activity herein is functioning to suppress the activity of TM4SF4 protein, which can be selected from the group consisting of compounds, peptides, peptide mimetics, and antibodies complementarily binding to TM4SF4 protein, but not always limited thereto.

The said peptide mimetics are the peptides or non-peptides inhibiting binding domain of TM4SF4 protein to suppress the activity of TM4SF4. The major residues of non-hydrolysable peptide analogues can be generated by using β-turn dipeptide core (Nagai et al. *Tetrahedron Lett* 26:647, 1985), keto-methylene pseudopeptides (Swenson et al. *J Med Chem* 29:295, 1986; and Ewenson et al. in Peptides: Structure and Function (Proceedings of the 9th American Peptide Symposium) Pierce Chemical Co. Rockland, Ill., 1985), azepine (Huffman et al. in Peptides: Chemistry and Biology, G. R. Marshall ed., ESCOM Publisher: Leiden, Netherlands, 1988), benzodiazepine (Freidinger et al. in Peptides; Chemistry and Biology, G. R. Marshall ed., ESCOM Publisher: Leiden, Netherlands, 1988), β-aminoalcohol (Gordon et al. *Biochem Biophys Res Commun* 126:419 1985), and substituted gamma lactam ring (Garvey et al. in Peptides: Chemistry and Biology, G. R. Marshell ed., ESCOM Publisher: Leiden, Netherlands, 1988).

The present inventors confirmed that the expression of TM4SF4 was higher in adenocarcinoma cell lines (A549, and Calu-3) than in other non-small cell lung cancer cell lines by reverse transcription polymerase chain reaction (RT-PCR) and Western blotting. It was also confirmed by colony formation analysis that cell growth was inhibited when the expression of TM4SF4 was suppressed by siRNA. It was also confirmed by transwell or wound healing experiment that migration and infiltration of the said cancer cell lines were reduced when the expression of TM4SF4 was suppressed. The present inventors further neutralized the activity of the protein by treating TM4SF4 antibody thereto. As a result, cell growth was suppressed by the treatment of anti-TM4SF4 antibody dose-dependently, confirmed by colony formation assay. When TM4SF4 was down-regulated, IGF1Rβ/PI3K-Akt/NK-κB activity that causes cell growth was decreased. In the meantime, when TM4SF4 was over-expressed by using TM4SF4 expression vector, the said signal transduction pathway was more activated. The present inventors also observed that the expressions of MMP (matrix metalloproteinase)-2, 7, and 9, which are necessary factors for angiogenesis essential for metastasis, were decreased when TM4SF4 was down-regulated. On the contrary, when TM4SF4 was up-regulated, the expressions of MMP-2, 7, and 9 were all increased. Therefore, the pharmaceutical composition comprising a substance inhibiting the expression and activity of TM4SF4 can be effectively used for the prevention and treatment of adenocarcinoma among non-small cell lung cancers by decreasing cell growth, metastasis, and infiltration of adenocarcinoma cells by suppressing the activations of IGF1Rβ/PI3K-Akt/NK-κB and MMP.

The present invention also provides an anticancer agent for adenocarcinoma among non-small cell lung cancers comprising an inhibitor of the expression or activity of TM4SF4 as an active ingredient.

The anticancer agent herein can increase radiosensitivity of adenocarcinoma cells among non-small cell lung cancer cells.

The radiation herein can be gamma radiation, X ray, or electron beam, and preferably gamma radiation, and more preferably $^{60}$Co γ-ray, but not always limited thereto.

The radiation dose herein is 0.2~20 Gy, preferably 0.5~10 Gy, and most preferably 2 Gy, but not always limited thereto. The irradiation rate herein is 0.02~2 Gy/min, preferably 0.05~1 Gy/min, and more preferably 0.2 Gy/min, but not always limited thereto.

To investigate whether or not the suppression of TM4SF4 expression could affect radiosensitivity of cells, the present inventors suppressed the expression of TM4SF4 in an adenocarcinoma cell line (A549) among non-small cell lung cancer cell lines by using siRNA complementary to TM4SF4 mRNA. Then, colony formation analysis was performed to investigate radioresistance of the cell line, specifically resistance of the cell line to gamma radiation. As a result, in A549 cell line demonstrating lower expression of TM4SF4, colony formation was significantly increased, suggesting that radioresistance of the cell line was reduced according to the down-regulation of TM4SF4, in other words radiosensitivity of the cell line was increased. Therefore, the TM4SF4 expression or activity inhibitor can be effectively used as an anticancer agent accompanied by radiotherapy since it can increase radiosensitivity of cancer cells by suppressing the expression or activity of TM4SF4 protein.

The composition of the present invention comprising an inhibitor of TM4SF4 expression or activity as an active ingredient can include the said active ingredient at the concentration of 0.0001~50 weight % by the total weight of the composition.

The composition of the present invention can include, in addition to the inhibitor of TM4SF4 expression or activity, one or more active ingredients having the same or similar function to the inhibitor of TM4SF4 expression or activity.

The composition of the present invention can also include, in addition to the above-mentioned active ingredients, one or more pharmaceutically acceptable carriers for the administration. The pharmaceutically acceptable carrier can be selected or be prepared by mixing more than one ingredients selected from a group consisting of saline, sterilized water, Ringer's solution, buffered saline, dextrose solution, maltodextrose solution, glycerol, ethanol, and liposome. Other general additives such as anti-oxidative agent, buffer solution, bacteriostatic agent, etc., can be added. The composition of the present invention can be formulated in different forms including aqueous solutions, suspensions and emulsions for injection, pills, capsules, granules or tablets by mixing with diluents, dispersing agents, surfactants, binders and lubricants. A target organ specific antibody or other ligands can be mixed with one of the said carriers to be delivered to the target organ. The composition can further be prepared in suitable forms according to ingredients by following the method represented in Remington's Pharmaceutical Science (the newest edition), Mack Publishing Company, Easton Pa.

The nucleotide or nucleic acid used in this invention can be formulated suitable for such administrations as oral, local, parenteral, intranasal, intravenous, intramuscular, hypodermic, ophthalmic or transdermal administration. It is more preferred for the nucleic acid or the vector to be formulated suitable for injection. To prepare the composition for direct injection, the composition can be mixed with any pharmaceutically acceptable mediate. The composition of the present invention can be formulated in the form of a lyophilized composition which is suitable for the preparation of an injectable solution by containing sterilized isotonic solution, sterilized water, or saline. Direct injection of the nucleic acid to a tumor of a patient is favorable because the treatment effect in directed to the infected area alone. Dose of the nucleic acid can be adjusted by various parameters, for example gene, vector, administration method, disease, and treatment period required, etc. In addition, weight, age, gender, health condition, diet, administration frequency, administration method, execretion, and severity of disease are also considered to adjust the dose. The effective dose is approximately 0.001~100 mg/kg/day, and preferably 0.01~10 mg/kg/day, which is administered once a day~a few times a day.

The present invention further provides a pharmaceutical composition for preventing and treating non-small cell lung cancers except adenocarcinoma comprising an expression vector harboring a gene encoding TM4SF4 protein as an active ingredient.

The expression vector containing the gene encoding TM4SF4 protein herein is composed of the gene sequence represented by SEQ. ID. NO: 2, but not always limited thereto. Any gene sequence modified by DNA deletion, addition, or substitution of one or more DNAs can be included as well, and preferably at this time, the gene sequence having at least 80% and more preferably at least 90% homology is preferred.

The vector herein can include either non-viral vector or viral vector. The non-viral vector herein includes linear DNA, plasmid DNA, and liposome, but not always limited thereto. The viral vector herein includes retrovirus, adenovirus, adeno-associated virus, and herpes virus, but not always limited thereto.

The present inventors confirmed through RT-PCR and Western blotting that the expression of TM4SF4 was lower in non-small cell lung cancer cell lines (H460, A431, H23, H1299, H2009, and H358) except adenocarcinoma cell lines (A549, and Calu-3) than in adenocarcinoma cell lines. To further the effect of the expression of TM4SF4 on cell growth, the present inventors performed colony formation analysis with non-small cell lung cancer cell lines except adenocarcinoma. Particularly, the inventors induced over-expression of TM4SF4 by using pcDNA3.1, the TM4SF4 expression vector. As a result, it was confirmed that cell growth was inhibited in non-small cell lung cancer cell lines except adenocarcinoma cells over-expressing TM4SF4. Therefore, it was concluded that the pharmaceutical composition comprising a substance capable of increasing the expression of TM4SF4 in non-small cell lung cancer cells except adenocarcinoma cells decreased cell growth therein, indicating that the composition could be effectively used for the prevention and treatment of non-small cell lung cancers except adenocarcinoma.

The present invention also provides an anticancer agent for non-small cell lung cancers except adenocarcinoma comprising an expression vector harboring a gene encoding TM4SF4 protein as an active ingredient.

The anticancer agent herein can increase radiosensitivity of non-small cell lung cancer cells except adenocarcinoma cells. The characteristics and irradiation method and dose of the applicable radiation are same as the above.

The non-small cell lung cancer except adenocarcinoma herein indicates that adenocarcinoma is excluded. More particularly, the non-small cell lung cancer includes squamouse cell carcinoma and large cell carcinoma, and more preferably it indicates large cell carcinoma, but not always limited thereto.

The concentration of the active ingredient, the recombinant expression vector expressing TM4SF4 gene represented by SEQ. ID. NO: 2, in the anticancer agent is preferably 0.01~50 weight % by the total weight of the anticancer agent composition, but not always limited thereto. The said anticancer agent can also include such additives as purified water, excipients, stabilizers, or preservatives in addition to the recombinant expression vector expressing TM4SF4.

The anticancer agent comprising the recombinant expression vector expressing TM4SF4 gene of the present invention can be prepared in a variety forms of formula such as tablets, capsules, injections, granules, and pills, for oral administration, injection, local treatment, or spreading.

The present invention also provides a composition for increasing radiosensitivity of adenocarcinoma cells among non-small cell lung cancer cells comprising an inhibitor of the expression or activity of TM4SF4 as an active ingredient.

The present invention also provides a composition for increasing radiosensitivity of non-small cell lung cancer cells except adenocarcinoma cells comprising an expression vector harboring a gene encoding TM4SF4 protein as an active ingredient.

The present invention also provides a method for increasing radiosensitivity of adenocarcinoma cells among non-small cell lung cancer cells comprising the step of administering an inhibitor of the expression or activity of TM4SF4 to adenocarcinoma cells among non-small cell lung cancer cells.

The present invention also provides a method for increasing radiosensitivity of non-small cell lung cancer cells except adenocarcinoma cells comprising the step of administering an expression vector containing TM4SF4 gene to non-small cell lung cancer cells except adenocarcinoma cells.

The radiation herein can be gamma radiation, X ray, or electron beam, and preferably gamma radiation, and more preferably $^{60}$Co γ-ray, but not always limited thereto.

The radiation dose herein is 0.2~20 Gy, preferably 0.5~10 Gy, and most preferably 2 Gy, but not always limited thereto. The irradiation rate herein is 0.02~2 Gy/min, preferably 0.05~1 Gy/min, and more preferably 0.2 Gy/min, but not always limited thereto.

The present invention also provides a method for screening an anticancer drug or an anticancer agent for non-small cell lung cancer comprising the following steps:

1) treating test materials to the cell line expressing TM4SF4 protein; and 2) selecting a substance that is able to regulate the expression or activity of TM4SF4 protein in the above cell line.

Particularly, the present invention provides a method for screening an anticancer drug or an enhancer candidate to increase radiosensitivity of adenocarcinoma cells among non-small cell lung cancer cells comprising the following steps:

1) treating test materials to the cell line expressing TM4SF4 protein;
2) measuring the expression or activity of TM4SF4 protein in the above cell line; and
3) selecting the test material demonstrating lower expression or activity of TM4SF4 protein than that of the control non-treated with the test material.

Particularly, the present invention provides a method for screening an anticancer drug or an enhancer candidate to increase radiosensitivity of non-small cell lung cancer cells except adenocarcinoma cells comprising the following steps:

1) treating test materials to the cell line expressing TM4SF4 protein TM4SF4;
2) measuring the expression or activity of TM4SF4 protein in the above cell line; and
3) selecting the test material demonstrating higher expression or activity of TM4SF4 protein than that of the control non-treated with the test material.

In the above two screening methods, the TM4SF4 protein of step 1) is composed of the amino acid sequence represented by SEQ. ID. NO: 1, but not always limited thereto.

In the above two screening methods, the expression of the said protein of step 2) can be measured by any method known to those in the art being used to measure the transcript or the protein encoded from the same, which is preferably selected from the group consisting of immunoprecipitation, RIA, ELISA, immunohistochemistry, RT-PCR, Western blotting, and FACS, but not always limited thereto. The activity of the said protein of step 2) can also be measured by one of those methods selected from the group consisting of SDS-PAGE, immunofluorescence, ELISA, mass spectrometry, and protein chip, but not always limited thereto.

In the above two screening methods, the radiation of step 3) can be gamma radiation, X ray, or electron beam, and preferably gamma radiation, but not always limited thereto.

In this invention, it was confirmed that cell growth, metastasis, infiltration, and radiosensitivity were changed according to the regulation of TM4SF4 expression in adenocarcinoma cells among non-small cell lung cancer cells, and in other non-small cell lung cancer cells. It was also confirmed in this invention that the above change is contrary between adenocarcinoma cells and other non-small cell lung cancer cells. More precisely, when the expression of TM4SF4 was down-regulated in adenocarcinoma cells, cell growth, metastasis, infiltration, and radioresistance were all reduced. On the contrary, when the expression of TM4SF4 was up-regulated in non-small cell lung cancer cells except adenocarcinoma cells, cell growth and radioresistance were reduced. Therefore, an anticancer drug or an anticancer agent bringing the effect of increasing radiosensitivity of adenocarcinoma cells among non-small cell lung cancer cells or non-small cell lung cancer cells except adenocarcinoma cells can be selected by screening a test material that can control the expression of TM4SF4.

The present invention also provides a method for treating adenocarcinoma among non-small cell lung cancers, comprising the step of administering a pharmaceutically effective dose of an inhibitor of TM4SF4 expression or activity to a subject having adenocarcinoma.

The present invention also provides a method for preventing adenocarcinoma among non-small cell lung cancers, comprising the step of administering a pharmaceutically effective dose of an inhibitor of TM4SF4 expression or activity to a subject.

The present invention also provides a method for treating non-small cell lung cancer except adenocarcinoma comprising the step of administering a pharmaceutically effective dose of an expression vector harboring a gene encoding TM4SF4 protein to a subject having non-small cell lung cancer except adenocarcinoma.

The present invention also provides a method for preventing non-small cell lung cancer except adenocarcinoma comprising the step of administering a pharmaceutically effective dose of an expression vector harboring a gene encoding TM4SF4 protein to a subject.

The present invention also provides a use of the inhibitor of TM4SF4 expression or activity as a pharmaceutical composition for the prevention and treatment of adenocarcinoma among non-small cell lung cancers.

The present invention also provides a use of the inhibitor of TM4SF4 expression or activity as an anticancer agent for adenocarcinoma among non-small cell lung cancers.

The present invention also provides a use of the expression vector containing the gene encoding TM4SF4 protein as a pharmaceutical composition for the prevention and treatment of non-small cell lung cancer except adenocarcinoma.

The present invention also provides a use of the expression vector containing the gene encoding TM4SF4 protein as an anticancer agent for non-small cell lung cancer except adenocarcinoma.

The present invention also provides a use of the inhibitor of TM4SF4 expression or activity as an enhancer of radiosensitivity of adenocarcinoma cells among non-small cell lung cancer cells.

In addition, the present invention also provides a use of the expression vector containing the gene encoding TM4SF4 as an enhancer of radiosensitivity of non-small cell lung cancer cells except adenocarcinoma cells.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Construction of TM4SF4 Expression Vector for Transfection

To construct the expression vector for human TM4SF4 gene, PCR was performed with genomic DNA of A549 cells over-expressing TM4SF4 using the primers [EcoRI/forward: 5'-CCACGAATTCATGTGCACTGGGGGC-3' (SEQ. ID. NO: 3), XhoI/reverse: 5'-TCCTCGAGTTAAACGGGTC-CATCTCCC-3' (SEQ. ID. NO: 4)]. At this time, a thermal cycler (APOLLO, San Diego, USA) was used. As a result, 626 bp sized TM4SF4 was obtained. PCR was induced with 1 µg of the genomic DNA, 1 µl of 10 pmol primer each, and PCR premix (Maxim™ PCR PreMix, i-Taq) (iNtRON Biotechnology, Sungnam, Korea). PCR was performed as follows; denaturation at 94° C. for 1 minute, annealing at 58.9° C. for 30 seconds, elongation at 72° C. for 1 minute, 30 cycles from denaturation to elongation, and post-elongation at 72° C. for 5 minutes.

The expression vector pcDNA3.1(+) was mixed with the restriction enzymes EcoRI and XhoI (Invitrogen), 1 μl each, and buffer, followed by reaction at 37° C. for at least 2 hours. The said expression vector, TM4SF4 DNA obtained from the above PCR, T4 ligase, and T4 buffer were mixed, followed by reaction at 16° C. for at least 2 hours. A diagram illustrating the construction of the said expression vector is presented in FIG. 1. DH5α (iNtRON biotechnology, Sungnam, Korea) E. coli, the host, and the constructed expression vector were mixed, which stood at 4° C. for 30 minutes. Then, heat-shock was given to the mixture at 42° C. for 90 seconds. The mixture was inoculated in SOC medium, followed by culture in a 37° C. shaking incubator for 1 hour. The culture mixture was smeared on LB solid medium supplemented with ampicillin as an antibiotic marker, followed by further culture in a 37° C. incubator for 16 hours. The obtained colonies were treated with the restriction enzymes EcoRI and XhoI (Invitrogen) to confirm the insertion of the DNA via sequencing. The colony confirmed to match 100% was cultured overnight in LB broth supplemented with ampicillin. Then, plasmid DNA was extracted therefrom by using DNA-spin plasmid DNA extraction kit (iNtRON biotechnology, Sungnam, Korea). A549, H460, A431, H23, H1299, H2009, H358, or Calu-3 cells were loaded in a 6 well plate at the density of $4 \times 10^5$ cells/well. For the efficient transfection, the medium was replaced with opti-MEM. 4 μg of the extracted TM4SF4/pcDNA3.1 DNA was mixed with 10 μl of lipofectamine 2000 (Invitrogen) for 20 minutes, which was added to the above cells. 5 hours later, the medium was replaced with RPMI1640 in order to grow the temporarily transfected cells. Next experiment was performed 72 hours later. The expression of TM4SF4 in the cells mediated by the TM4SF4 expression vector was confirmed by RT-PCR.

Example 1

Confirmation of TM4SF4 Over-Expression in the Adenocarcinoma Cell Lines A549 and Calu-3 by RT-PCR and Western Blotting To investigate the expression of TM4SF4 in various lung cancer cell lines including adenocarcinoma cell line, RT-PCR and Western blotting were performed to quantify TM4SF4 mRNA and protein.

For RT-PCR, reaction mixture was prepared in the total volume of 20 al including 1 μg of total RNA and Maxim™ RT PreMix-Oligo(dT)15Primer (iNtRON biotechnology, Sungnam, Korea). Reaction was then induced at 45° C. for 60 minutes and at 95° C. for 5 minutes and as a result the RT-PCR product cDNA was synthesized. Reaction mixture was prepared in the total volume of 20 al by mixing the synthesized cDNA as a template, 1 al of TM4SF4 primer [forward: 5'-CCACGAATTCATGTGCACTGGGGGC-3 (SEQ. ID. NO: 3)', reverse: 5'-TCCTCGAGTTAAACGGGTC-CATCTCCC-3' (SEQ. ID. NO: 4)] or β-actin primer [forward: 5'-CATCCTCACCCTGAAGTACCC-3' (SEQ. ID. NO: 5), reverse: 5'-AGCCTGGATAGCAACGTACATG-3' (SEQ. ID. NO: 6)], 16 al of sterilized water, and PCR premix (Maxim™ PCR PreMix, i-Taq) (iNtRON biotechnology, Sungnam, Korea). PCR was performed as follows using a thermal cycler (APOLLO, San Diego, USA); denaturation at 94° C. for 1 minute, annealing at 58.9° C. for 30 seconds, elongation at 72° C. for 1 minute, 30 cycles from denaturation to elongation, and post-elongation at 72° C. for 5 minutes. The PCR product was electrophoresed on 1% agarose gel, followed by staining with EtBr (Ethidium Bromide) for observation.

Cell culture was performed in RPMI 1640 supplemented with 10% fetal bovine serum (FBS, Hyclone) and antibiotics (100 U/ml penicillin and 100 μg/ml streptomycin, Hyclone) in a 37° C., 5% $CO_2$ incubator. $1 \times 10^7$ cells of A549, H460, A431, H23, Calu-3, H1299, H2009, or H358 were obtained and washed twice with PBS. The cells were suspended in RIPA buffer containing protease inhibitor cocktail (2 mM AEBSF, 1 mM EDTA, 130 μM bestatin, 1 μM leupeptin, 14 μM E-64, and 0.3 μM aprotinin) and phosphatase inhibitor, which stood in ice for 20 minutes, followed by quick vortexing 3 times. Then, centrifugation was performed at 12,000 rpm, at 4° C. for 20 minutes to obtain supernatant. Centrifugation was performed again at 12,000 rpm, at 4° C., for 20 minutes. As a result, pure supernatant was obtained. The protein contained in the supernatant was quantified by Lowry method. Electrophoresis was performed with 40 μg of whole cell lysate on 7.5~12% acrylamide gel (Bio-rad, Japan) at 80 V for 1 hour and then at 100 V for 90 minutes. The protein isolated by the above electrophoresis was transferred onto PVDF membrane (polyvinyledene floride membrane) (Bio-Rad, USA) which was soaked in 100% methanol for 10 seconds and then hydrated fully with distilled water by using semi-dry transfer (Bio-Rad, USA) at 20 V for 1 hour. The membrane was reacted with blocking buffer (5% BSA, 0.1% Tween-20/TBS) at room temperature for 1 hour to remove non-specific binding. Then, the membrane was reacted with the primary antibody, anti-TM4SF4 antibody (abcam, #ab102946), and anti-β-actin antibody (Sigma-Aldrich, #A3854) at 4° C. overnight for conjugation. The membrane was further reacted with the secondary antibodies, peroxidase-conjugated anti-IgG antibodies (Cell-signaling, #7076 and #7074) at room temperature for 1 hour. Color development was examined by using ECL detection kit (Amersham, UK) to investigate the expression of TM4SF4, and the result is presented in FIG. 1. β-actin was used as the loading control. The equal amount of β-actin indicates the equal amount of protein was loaded.

Figure 2:
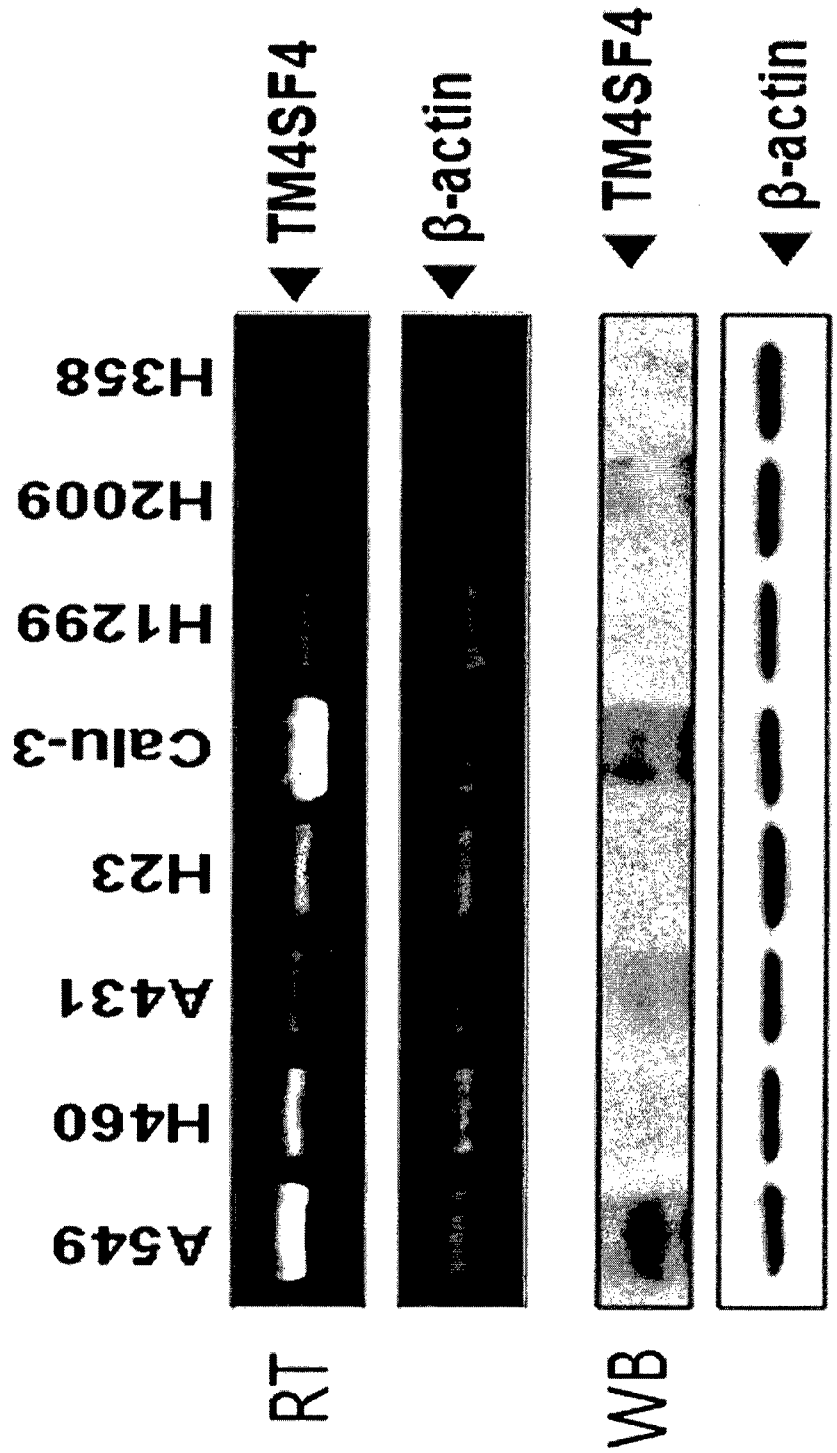
FIG. 2 is a diagram illustrating TM4SF4 (transmembrane 4 L six family member 4) expression in various lung cancer cell lines (A549/H460/A431/H23/H1299/H2009/H358/Calu-3), confirmed by RT-PCR and Western blotting (WB).

The results of RT-PCR and Western blotting all demonstrated up-regulated TM4SF4 at mRNA level and at protein level as well, in the adenocarcinoma cell lines A549 and Calu-3. On the other hand, TM4SF4 was comparatively down-regulated at mRNA level and at protein level as well, in other lung cancer cell lines (H460, A431, H23, 1299, H2009, and H358) (FIG. 2).

Example 3

Decrease of Cell Growth and Radioresistance by TM4SF4 Over-Expression in the Large Cell Carcinoma Cell Lines H1299 and H460 Among Lung Cancer Cell Lines, Confirmed by Colony Formation Assay According to the results of Example 2, adenocarcinoma cell line and non-adenocarcinoma cell line demonstrated different TM4SF4 expression patterns, even though they are all lung cancer cell lines. Therefore, cell growth and radioresistance in the large cell carcinoma cell lines H1299 and H460 among many lung cancer cell lines were first observed to examine how they were related to TM4SF4 expression and to investigate the functions of TM4SF4. More particularly, it was investigated by colony formation assay how cell growth and radiosensitivity of large cell carcinoma cells were changed when TM4SF4 was down-regulated by using siRNA technique and when TM4SF4 was over-expressed by TM4SF4/pcDNA3.1 transfection. The number of colonies was counted and presented as colony survival rate (%) by that of the control.

<3-1> Confirmation of Cell Growth Inhibition by TM4SF4 Over-Expression in H1299 and H460

$2 \times 10^3$ cells of H1299 or H460 were cultured in a 35-mm cell culture vessel, followed by transient transfection with 4 μg of the expression vector TM4SF4/pcDNA3.1 obtained in Example 1 and lipofectamine 2000 by the same manner as described in Example 1. 8 days later, live cells were stained with 0.5% (w/v) crystal violet solution, followed by observation. An empty vector was used for control.

Figure 3:
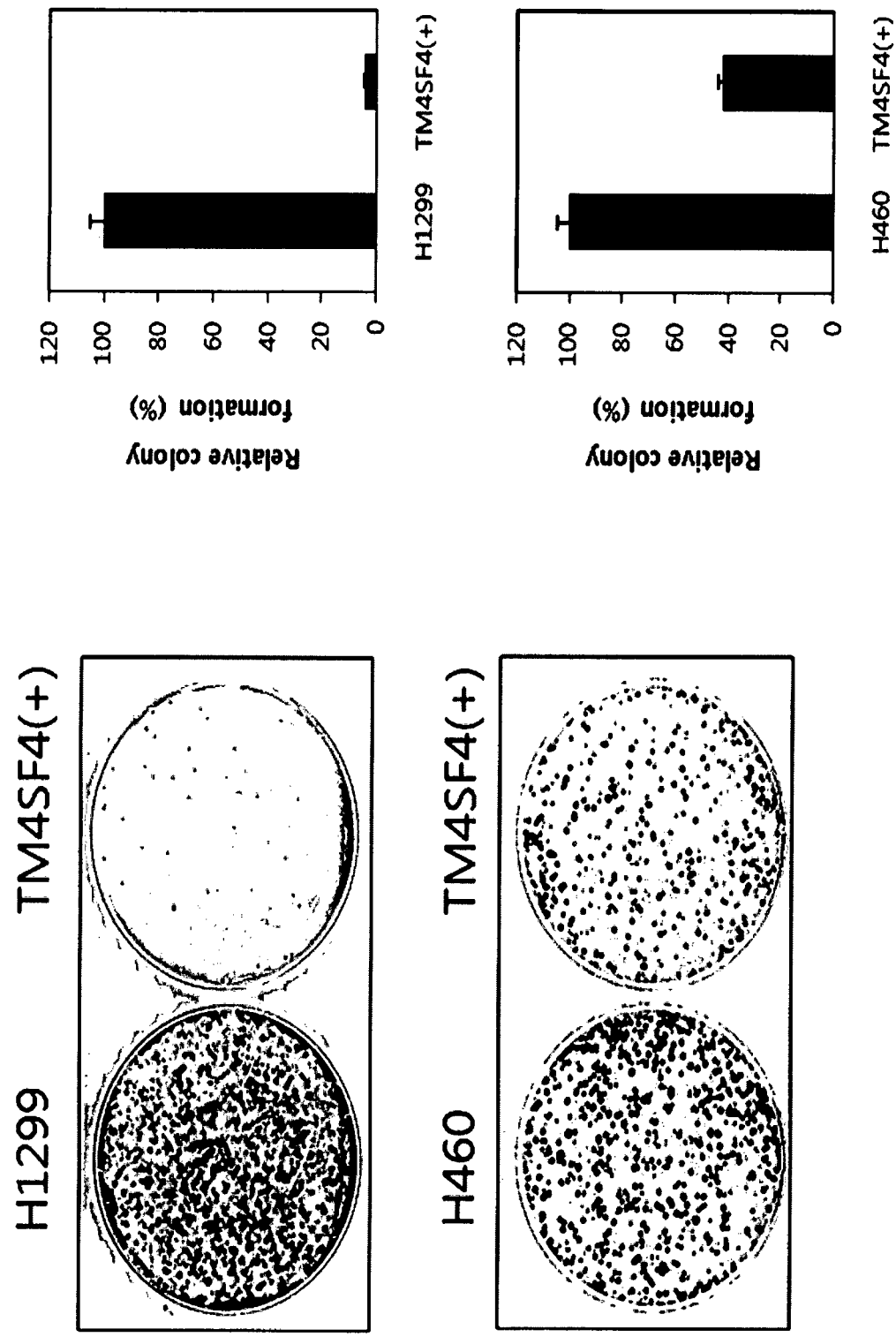
FIGS. 3~4 are diagrams illustrating the results of colony formation analysis performed to investigate cell growth (FIG. 3) and radiosensitivity (FIG. 4) in large cell carcinoma cell lines H1299 and H460 among many non-small cell lung cancer cell lines according to the over-expression of TM4SF4.

As a result, when TM4SF4 was over-expressed in the large cell carcinoma cell lines H1299 and H460, colonies of H1299 and H460 were significantly reduced, compared with those of the control (FIG. 3). That is, cell growth was inhibited by the over-expression of TM4SF4.

<3-2> Confirmation of the Decrease of Cell Growth and the Increase of Radiosensitivity by the Over-Expression of TM4SF4 in H460 Cells To over-express TM4SF4 in H460 cells, the experiment was performed by the same manner as described in Example 3-1. To investigate radiosensitivity, TM4SF4 was over-expressed by the same manner as described in Example 3-1. 72 hours later, cells were collected, followed by irradiation. Irradiation was performed with $^{60}$Co γ-ray at 0.2 Gy/min (2 Gy total). The cells were cultured in a 36° C., 5% $CO_2$ incubator for 8 days. Then, live cells were stained with 0.5% (w/v) crystal violet solution, followed by observation.

Figure 4:
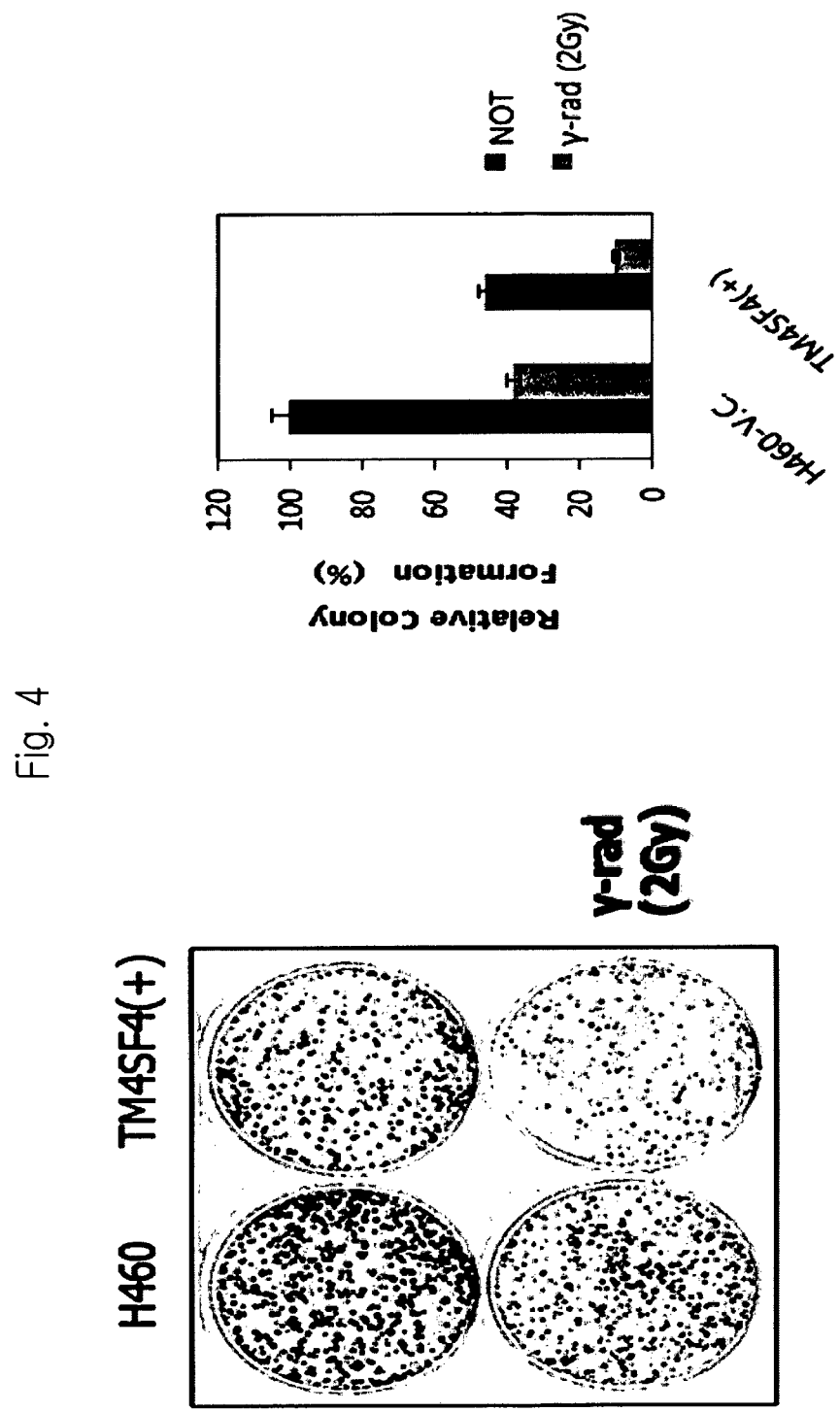

As a result, as confirmed in Example 3-1, when TM4SF4 was over-expressed in H460 cells, cell growth was inhibited (FIG. 4, up). When H460 cells over-expressing TM4SF4 were irradiated with 2 Gy of $^{60}$Co γ-ray, the number of colonies was significantly reduced, compared with that of the control (FIG. 4, down). Therefore, it could be concluded that when TM4SF4 was over-expressed in H460 cells, cell growth was inhibited but radiosensitivity was increased, which means radioresistance was reduced.

<3-3> Confirmation of the Increase of Cell Growth and the Decrease of Radiosensitivity by the Low-Expression of TM4SF4 in H460 Cells To down-regulate TM4SF4, TM4SF4-siRNA duplex oligoribonucleotide primers capable of suppressing the expression of TM4SF4 gene were constructed as 5'-gccucucaaugug-guucccuggaau-3' (SEQ. ID. NO: 7: sense)/5'-auuccagggaaccacauugagaggc-3' (SEQ. ID. NO: 8: antisense), which were functioning to suppress the gene expression by targeting a part of TM4SF4 gene (SEQ. ID. NO: 9). Stealth™ RNA targeting TM4SF4 (Invitrogen) was transiently transfected into cells using Lipofectamine™ RNAi MAX reagent (Invitrogen) by the same manner as described in Example 1. 72 hours later, the cells were collected and irradiated. Irradiation and colony formation assay thereafter were performed by the same manner as described in Example 3-2. The control cells were transfected with Lipofectamine™ RNAi MAX reagent alone.

Figure 5:
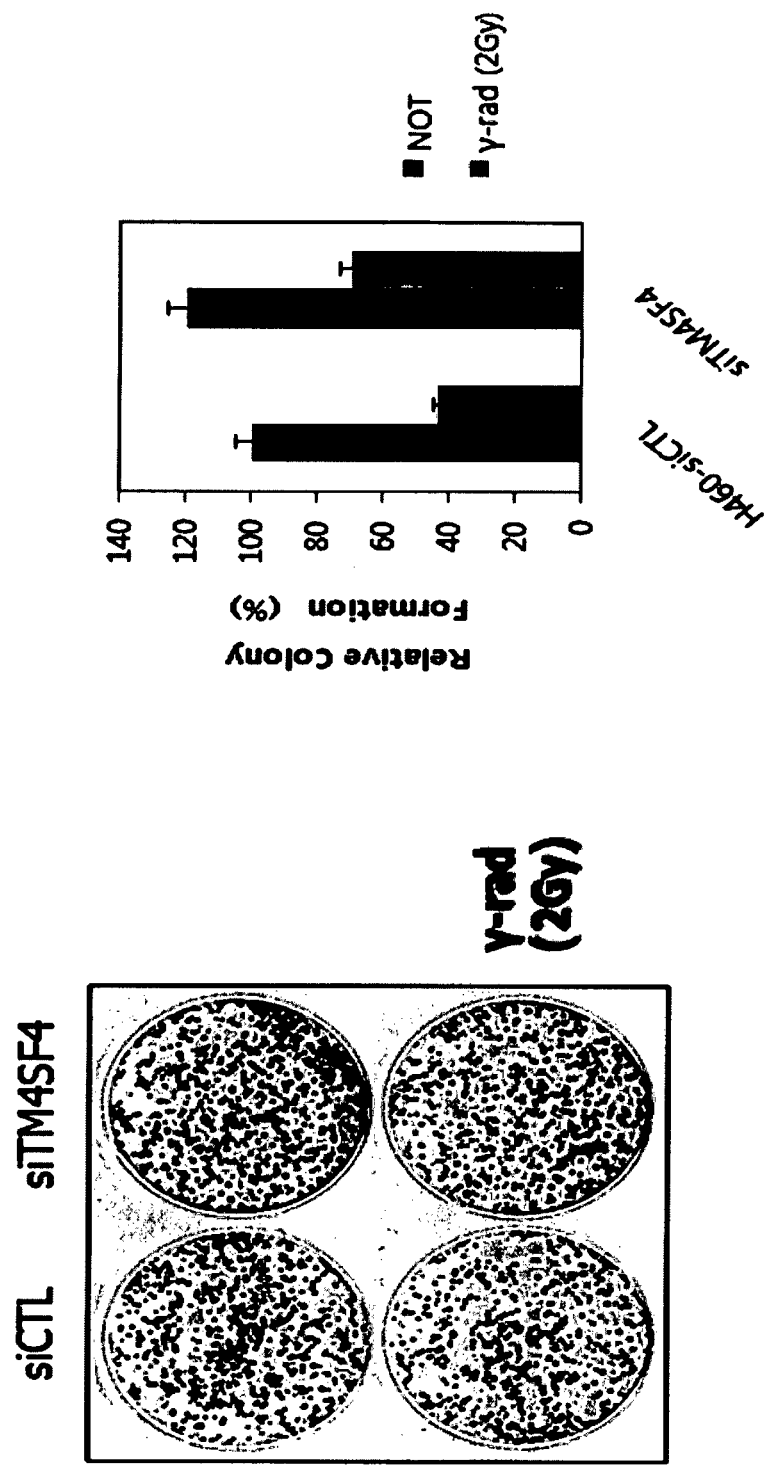
FIG. 5 is a diagram illustrating the result of colony formation analysis performed to investigate cell growth and radiosensitivity in H460 cells according to the down-regulation of TM4SF4.

As a result, when TM4SF4 was down-regulated in H460 cells, the number of colonies grown was increased, compared with that of the control (FIG. 5, up). When 2 Gy of $^{60}$Co γ-ray was irradiated, the number of colonies was increased (FIG. 5, down). That is, when TM4SF4 was down-regulated in the said cells, not only cell growth but also radioresistance were increased, in other words, radiosensitivity was reduced.

Example 4

Increase of Cell Growth and Radioresistance by the Low-Expression of TM4SF4 in the Adenocarcinoma Cell Line A549 Among Lung Cancer Cell Lines, Confirmed by Colony Formation Assay In the adenocarcinoma cell line A549 demonstrating comparatively low TM4SF4 expression, compared with those of other lung cancer cell lines, cell growth and radiosensitivity were investigated according to the changes of TM4SF4 expression by the following experiment.

The method to lower the expression of TM4SF4 in A549 cells by using TM4SF4 siRNA and colony formation assay to measure the cell growth and radiosensitivity and the method to present the results with survival rate (%) were all the same as described in Example 3-3.

Figure 6:
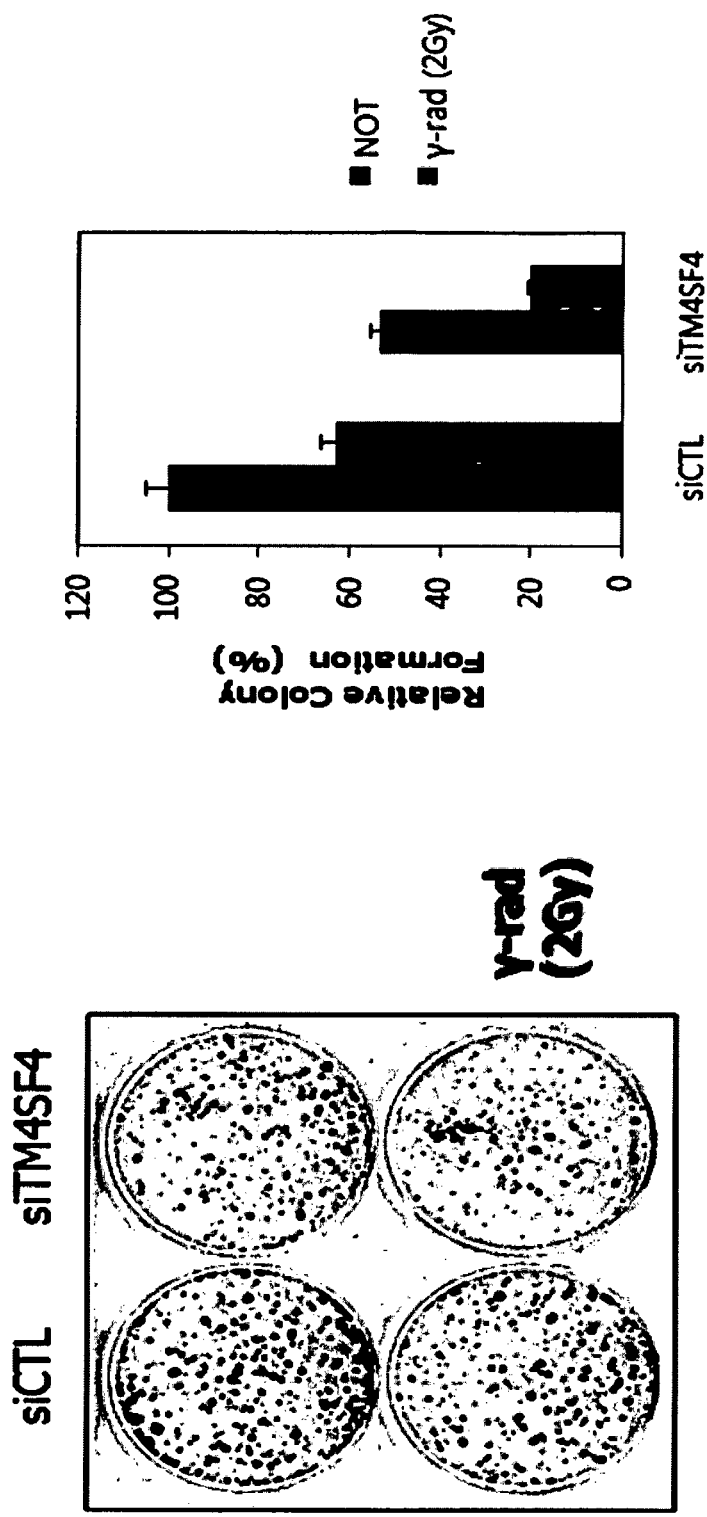
FIG. 6 is a diagram illustrating the result of colony formation analysis performed to investigate cell growth and radiosensitivity in the adenocarcinoma cell line A549, among many lung cancer cell lines, according to the down-regulation of TM4SF4.

As a result, unlike the results demonstrated in large cell carcinoma, among many types of lung cancers, when TM4SF4 was down-regulated in the adenocarcinoma cell line A549, the number of colonies cultured after irradiation was reduced (FIG. 6). The result indicates that when TM4SF4 that was over-expressed in the adenocarcinoma cell line A549 was suppressed, cell growth was inhibited and radioresistance was reduced, in other words, radiosensitivity was increased.

Example 5

Decrease of the Activity of Intracellular Signal Pathway by the Low-Expression of TM4SF4 in the Adenocarcinoma Cell Line A549 Among Lung Cancer Cell Lines, Confirmed by Western Blotting Based on the results confirmed above that the down-regulation of TM4SF4 could inhibit cell growth but increase radiosensitivity in the adenocarcinoma cell line A549, the following experiment was performed to investigate whether or not the activation of intracellular signal pathway mediating cell growth could affected by the expression of TM4SF4. Intracellular signal pathway is composed of many proteins linked stepwise and the activation thereof is mediated generally by phosphorylation of serine, threonine, and tyrosine residues. Thus, the level of phosphorylation means the level of activation thereof. In this example, phosphorylations of proteins mediating various intracellular signal pathways were measured by Western blotting when TM4SF4 was over-expressed and down-regulated.

As described in Example 3-3, TM4SF4 was down-regulated by using siRNA. Then, the activities of several intracellular signal pathways over-expressed in cancer cells were investigated. For example, phosphorylations of EGFR (epidermal growth factor receptor) known to regulate DNA synthesis, cell phenotype such as proliferation, migration and adhesion, IGF1Rβ (insulin-like growth factor 1 receptor β) known to have anti-apoptotic characteristics and to affect cell survival, proliferation, and migration, and to increase sensitivity to anticancer chemotherapy and radiotherapy, and PI3K (phosphatidylinositol 3 kinase) forming the intracellular signaling system of the above (for example, PTEN, Akt), and the transcription factors NK-kB and ERK were investigated. Phosphorylation of each signal pathway was investigated by Western blotting by the same manner as described in Example 2. The results of phosphorylation of EGFR, IGF1Rβ, PI3K, NK-κB, or ERK in each cell in the rich or lack of TM4SF4 or with no stimulus at all were confirmed by Western blotting using each antibody (Cell signaling, USA) and presented in FIG. 5.

Figure 7:
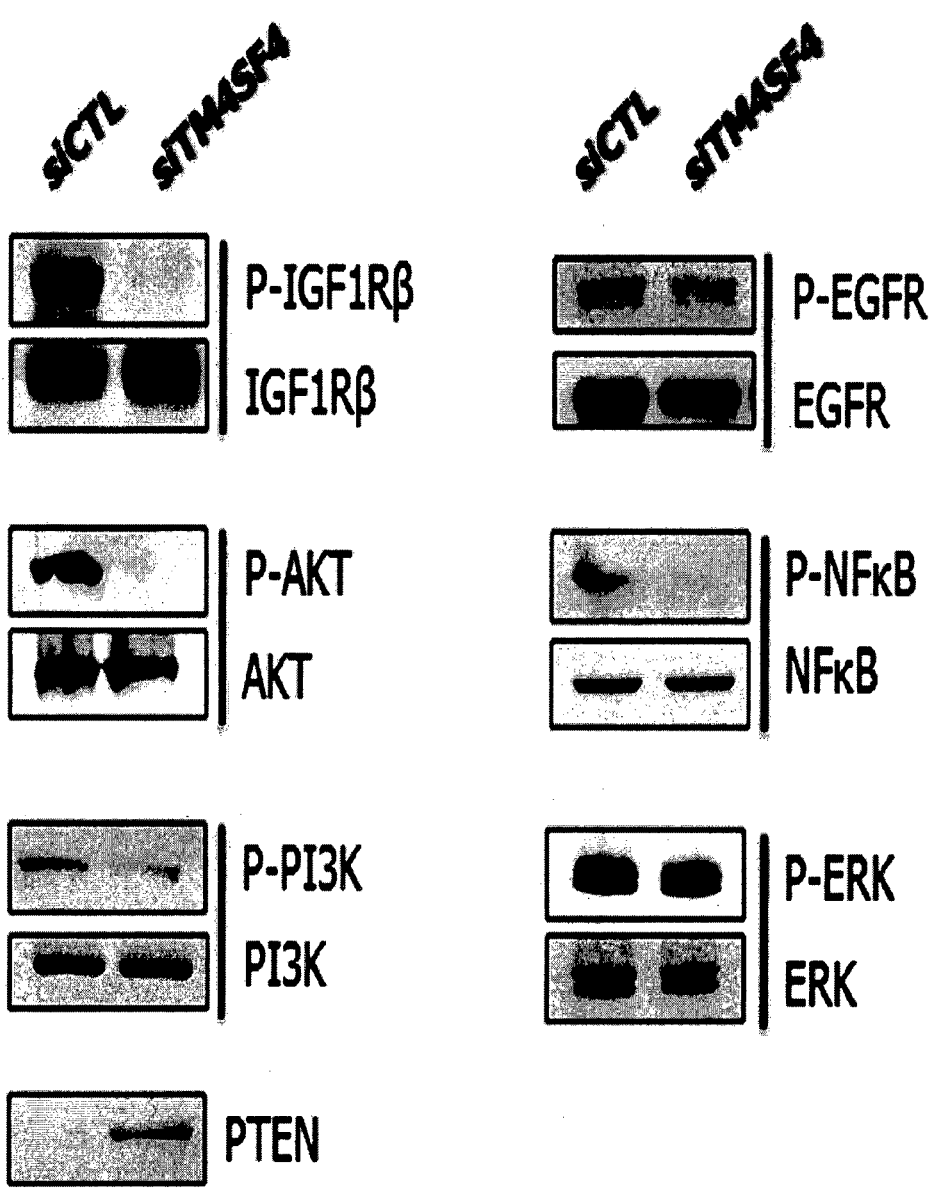
FIG. 7 is a diagram illustrating the result of Western blotting performed to investigate the phosphorylations of intracellular signals (IGF1R/PI3K/Akt/NF-κB, EGFR, ERK), related to cell growth and resistance, in both A549 cells with suppressed TM4SF4 and the control A549 cells.

As a result, it was confirmed that the activations of EGFR, IGF1Rβ, and PI3K mediating signal pathway important for cell growth and radiosensitivity were inhibited by the down-regulation of TM4SF4 (FIG. 7). Consistently with the above result, PTEN responsible for dephosphorylation of PI3K was activated by the down-regulation of TM4SF4 (FIG. 7). However, the activation of ERK was not affected much by the change of TM4SF4 expression (FIG. 7). That is, the low-expression of TM4SF4 could inhibit phosphorylations of EGFR, IGF1R, and PI3K, so that it can control cellular events involved in the activation of intracellular signal transduction pathway in relation to cell growth, etc.

Example 6

Decrease of Cell Migration by the Low-Expression of TM4SF4 in the Adenocarcinoma Cell Line A549 Among Lung Cancer Cell Lines, Confirmed by Wound Healing Test Following experiment was performed to investigate whether or not the expression of TM4SF4 could change cell growth or migration.

As described in Example 3-3, the low-expression of TM4SF4 was induced in A549 cells by using siRNA. 72 hours later, the cells were transferred in a 35-mm cell culture vessel, and cultured until confluency reached at least 90%. The cells were fully washed with PBS and the culture medium was replaced with RPMI 1640 supplemented with 0.5% FBS, followed by further culture overnight in a 5% $CO_2$, 37° C. incubator, which made starvation condition for the cells. After raking the cells on the floor of the vessel with a 200 µl tip, PBS was poured to wash it, in which the cell culture solution was filled in for further culture. Then, the distance between the cells was measured at the time points of 0 hr, 24 hr, and 36 hr. The distance was presented as % by that of the control.

As a result, migration of A549 cells with suppressed TM4SF4 was similar to that of the control up to the time point of 24 hr, but migration has been significantly decreased over the time since then, unlike the control in which migration was continuously increased up to the time point of 36 hr (FIG. 8). Therefore, it was confirmed in this invention that the expression of TM4SF4 played an important role in the continuous migration of A549 cells, the adenocarcinoma cell line.

Example 7

Decrease of Migration and Infiltration of the Adenocarcinoma Cell Line A549 Among Lung Cancer Cell Lines by the Low-Expression of TM4SF4, Confirmed by Transwell Examination Based on the results obtained in Example 6, it was investigated by using transwell how cell migration was affected by the expression of TM4SF4. In addition, it was also investigated by using transwell whether or not infiltration was changed according to the expression of TM4SF4. Cell migration and infiltration are necessary factors for cancer cell metastasis. Therefore, this experiment was to disclose how TM4SF4 expression affected not just cell migration but also cancer cell metastasis as well.

<7-1> Confirmation of the Decrease of Cell Migration By the Low-Expression of TM4SF4 in A549 Cells To observe cell migration, the expression of TM4SF4 was first down-regulated by using siRNA in A549 cells by the same manner as described in Example 3-3. 72 hours later, the cells were cultured in RPMI 1640 supplemented with 10% fetal bovine serum (FBS, Hyclone) and antibiotics (100 U/ml penicillin and 100 µg/ml streptomycin, Hyclone), which was loaded in chambers of a transwell (Cell biolabs) at the density of $2\times10^5$/300 µl. Lower chamber was filled with FBS-free RPMI 1640 (500 µl), followed by culture in a 5% $CO_2$, 37° C. incubator for 24 hours. Upon completion of the culture, the cells were stained with CyQuant® GR in order to observe cell migration down to the lower chamber of the transwell. The number of cells observed in the field was counted, which was presented as % by the control.

As a result, compared with the control, cell migration of the adenocarcinoma cell line A549 was approximately 30% decreased by the low-expression of TM4SF4 (FIG. 9, up). This result is consistent with that of Example 6.

<7-2> Confirmation of the Decrease of Cell Infiltration by the Low-Expression of TM4SF4 in A549 Cells To measure cell infiltration, the expression of TM4SF4 was first down-regulated by using siRNA in A549 cells by the same manner as described in Example 3-3. 72 hours later, $5\times10^5$ A549 cells were distributed in the upper transwell coated with 10 µl of Matrigel™ and dried. The cells were cultured in FBS-free RPMI 1640 at room temperature for 30 minutes. Then, the experiment using transwell was performed by the same manner as the one used for measuring cell migration above in Example 7-1. Upon completion of the culture, upper surface of each well was removed with by cotton swab and the cells were stained with CyQuant® GR in order to observe cell infiltration. The number of cells shown in the field was counted, which was presented as % by the control.

As a result, cell infiltration was approximately 40% decreased by the low-expression of TM4SF4 in the adenocarcinoma cell line A549 (FIG. 9, down). Therefore, it was confirmed in this example that the expression of TM4SF4 in the adenocarcinoma cell line A549 increased cell migration and infiltration, suggesting that the expression of TM4SF4 played an important role in promoting cancer cell metastasis.

Example 8

Decrease of MMP (Matrix Metalloprotease) Expression by the Low-Expression of TM4SF4 in the Adenocarcinoma Cell Line A549 Among Lung Cancer Cell Lines, Confirmed by Western Blotting To examine how the expression of TM4SF4 could affect angiogenesis essential for metastasis, the expression of MMP was investigated. MMP is a kind of protease that decomposes extracellular matrix and is known as one of essential factors for angiogenesis.

First, the expression of TM4SF4 was down-regulated by using siRNA in A549 cells by the same manner as described in Example 3-3. 72 hours later, whole cell lysate free from any stimulus was obtained by the same manner as described in Example 2, which proceeded to Western blotting by using each corresponding antibody (R&D system, USA) to measure the expressions of MMP-2. 7, and 9. β-actin was used as the loading control.

As a result, the expressions of MMP-2, 7, and 9 were significantly reduced by the suppression of TM4SF4 expression (FIG. 10). That is, TM4SF4 could control the expressions of intracellular MMP-2, 7, and 9.

Example 9

Decrease of Cell Growth and Radioresistance of the Adenocarcinoma Cell Line A549 Among Lung Cancer Cell Lines by the Over-Expression of TM4SF4

To over-express TM4SF4 in A549 cells, the method using TM4SF4/pcDNA3.1 expression vector, colony formation assay to measure cell growth and radiosensitivity, and the method to present the results as survival rate (%) were performed by the same manner as described in Example 3-2.

Figure 11:
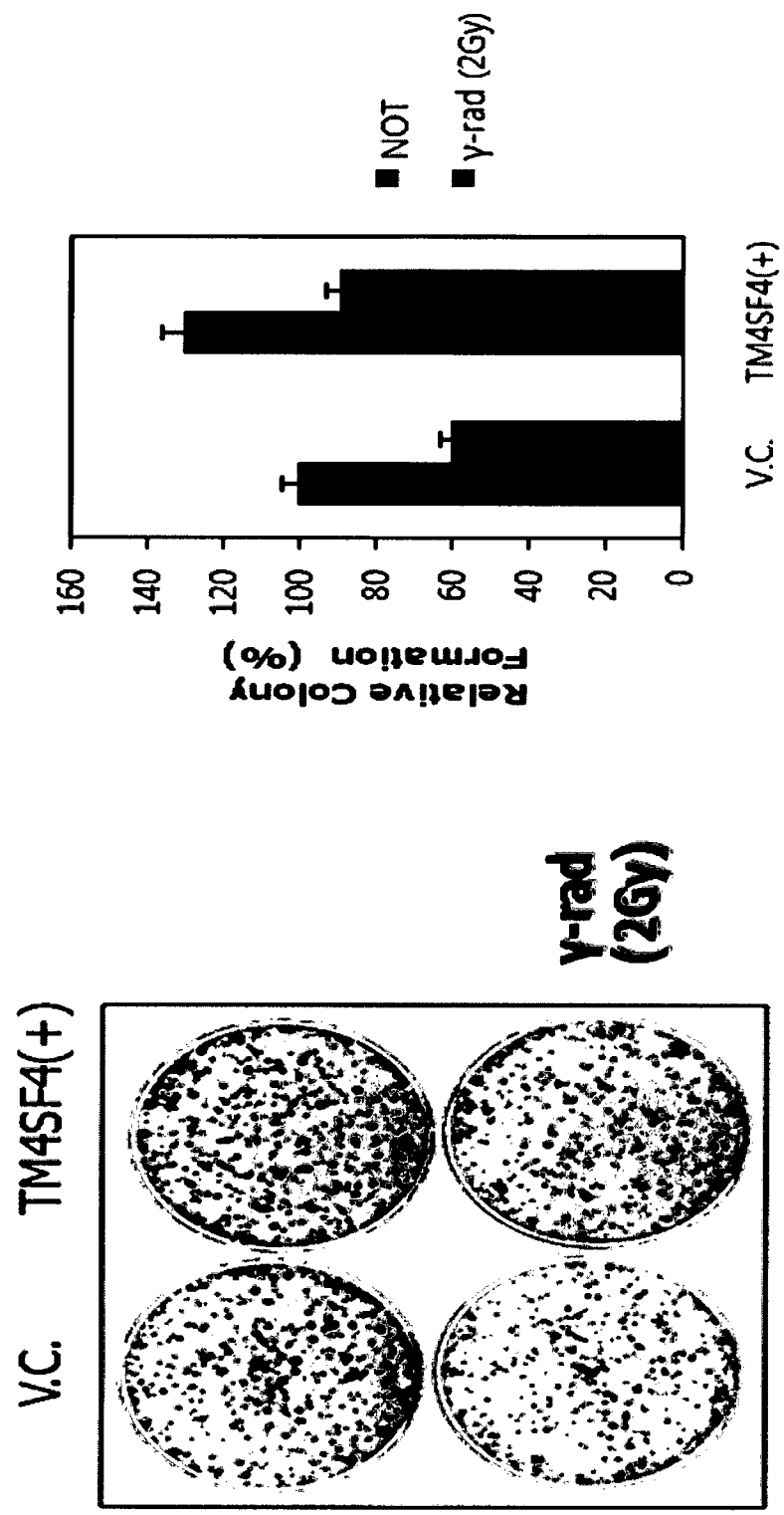
FIG. 11 is a diagram illustrating the result of colony formation analysis performed to investigate the cell growth and radioresistance in A549 cells according to the over-expression of TM4SF4.

As a result, unlike the result shown in large cell carcinoma, the number of colony was increased by the over-expression of TM4SF4 and by irradiation as well (FIG. 11). This result was consistent with that of Example 4. That is, the over-expression of TM4SF4 in the adenocarcinoma cell line A549 resulted in the increase of cell growth and radioresistance.

Example 10

Increase of the Activation of Intracellular Signal Pathway by the Over-Expression of TM4SF4 in the Adenocarcinoma Cell Line A549, Confirmed by Western Blotting As shown in Examples 4 and 5, the low-expression of TM4SF4 brought the effect of inhibiting intracellular signal pathway activation that is responsible for cell growth and radioresistance, which means the low-expression of TM4SF4 resulted in the decrease of cell growth and radioresistance. In this example, it was investigated whether or not the over-expression of TM4SF4 could affect the activation of intracellular signal pathway (EGFR, IGF1Rβ, PI3K, NK-κB, and ERK).

The over-expression of TM4SF4 was induced in A549 cells by the same manner as described in Example 3-2. The activation of intracellular signal pathway was investigated by the same manner as described in Example 5.

Figure 12:
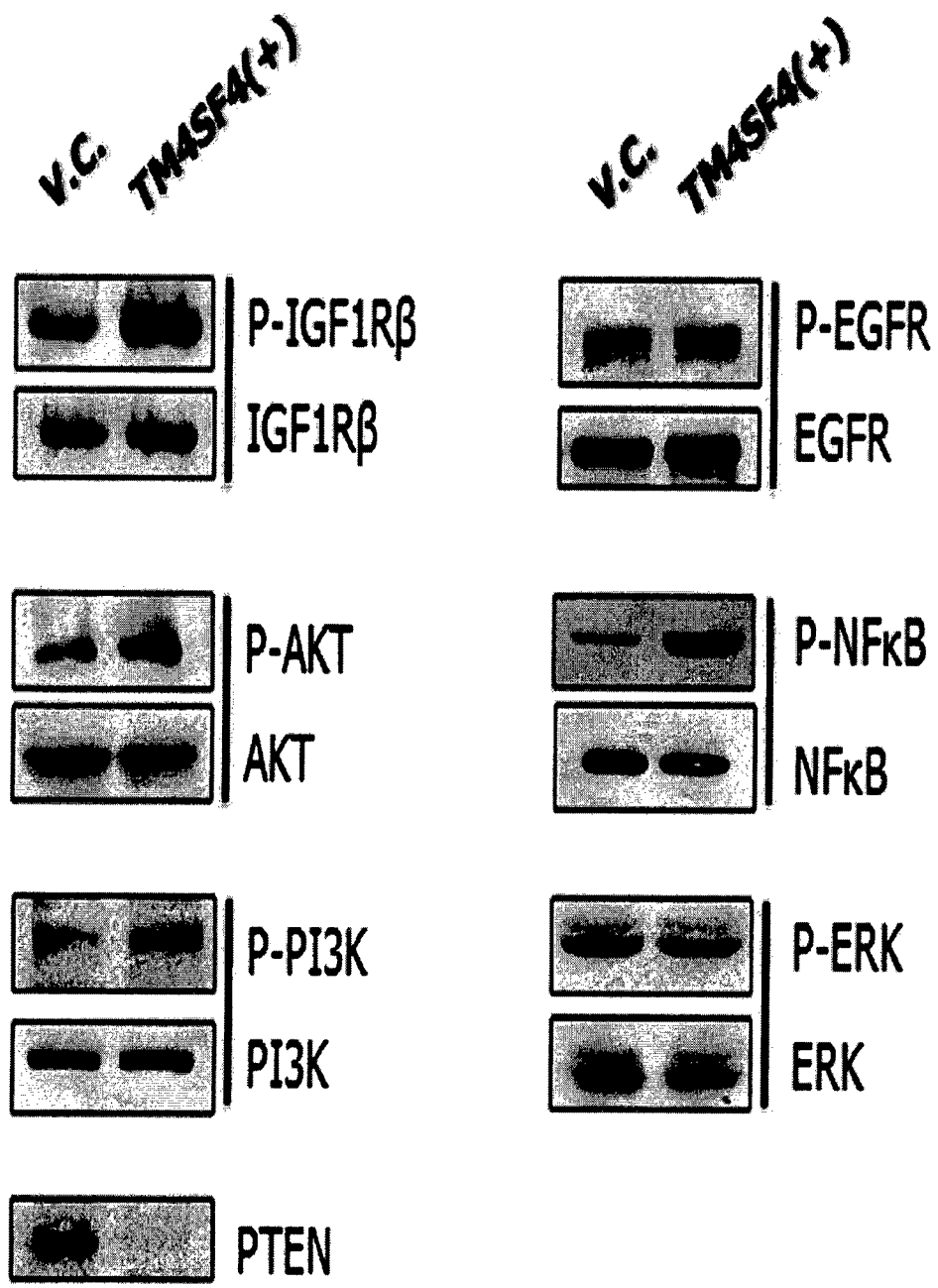
FIG. 12 is a diagram illustrating the result of Western blotting of IGF1R, PI3K/PTEN/Akt, NF-κB, ERK, and EGFR, performed to investigate the markers related to cell growth and resistance in A549 cells with over-expressed TM4SF4.

As a result, The over-expression of TM4SF4 in the adenocarcinoma cell line A549 resulted in the increase of phosphorylations of IGF1Rβ, PI3K, and NK-κB, but did not affect the activations of EGFR and ERK (FIG. 12). In conclusion, the over-expression of TM4SF4 increased the activations of IGF1Rβ, PI3K, and NK-κB, resulting in the increase of cell growth and radioresistance as shown in Example 9.

Example 11

Increase of Cell Migration by the Over-Expression of TM4SF4 in the Adenocarcinoma Cell Line A549 Among Lung Cancer Cell Lines, Confirmed by Wound Healing Test As shown in Example 6, the low-expression of TM4SF4 in A549 cells resulted in the decrease of cell migration. To confirm the above result again, it was investigated in this example whether or not cell migration could be changed by the over-expression of TM4SF4 in the same cell line, the adenocarcinoma cell line A549.

The method to induce the over-expression of TM4SF4 in A549 cells was the same as the one used in Example 3-2. To observe cell migration through wound healing process, cell migration was measured by the same manner as described in Example 6.

As a result, when TM4SF4 was over-expressed in the adenocarcinoma cell line A549, the distance between wounded cells was narrowed 24 hours later, compared with that of the control (FIG. 13). Therefore, it was confirmed that the over-expression of TM4SF4 in A549 cells increased cell migration.

Example 12

Increase of Cell Migration and Infiltration in the Adenocarcinoma Cell Line A549 Among Lung Cancer Cell Lines by the Over-Expression of TM4SF4, Confirmed by the Experiment Using Transwell Transwell was used in this example to investigate how cell migration and infiltration was affected by the over-expression of TM4SF4.

<12-1> Increase of Cell Migration by the Over-Expression of TM4SF4 in A549 Cells The over-expression of TM4SF4 was induced in A549 cells by using the expression vector TM4SF4/pcDNA3.1 by the same manner as described in Example 3-2. Then, cell migration was observed using transwell by the same manner as described in Example 7-1.

Figure 14:
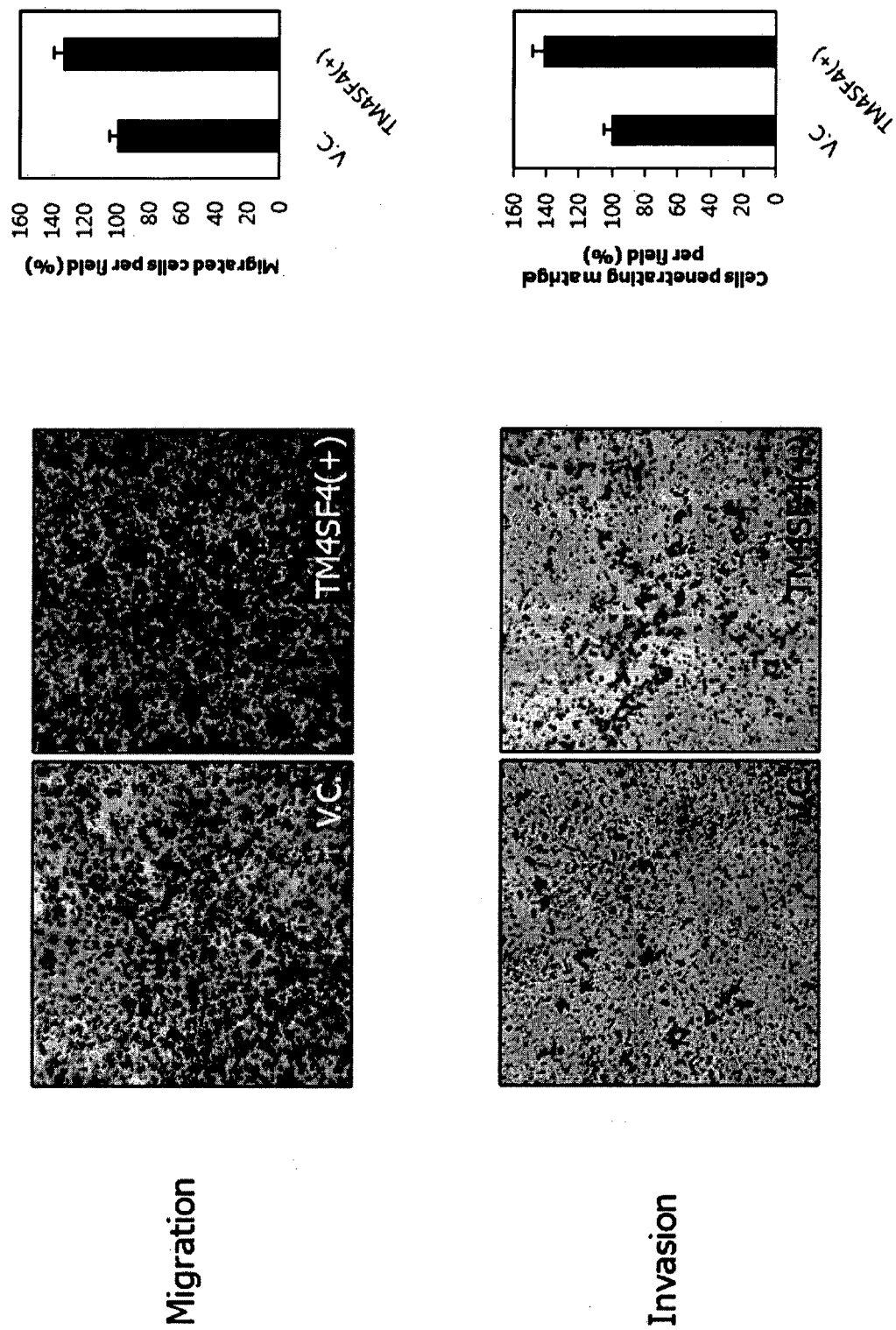
FIG. 14 is a diagram illustrating the result of H&E (hematoxylin & eosin) staining performed to investigate cell migration and infiltration induced by TM4SF4 over-expression in A549 cells.

As a result, when TM4SF4 was over-expressed in the adenocarcinoma cell line A549, cell migration was approximately 30% increased, compared with that of the control (FIG. 14, up).

<12-2> Increase of Cell Infiltration by the Over-Expression of TM4SF4 in A549 Cells The over-expression of TM4SF4 was induced in A549 cells by using the expression vector TM4SF4/pcDNA3.1 by the same manner as described in Example 3-2. Then, cell infiltration was observed using transwell by the same manner as described in Example 7-2.

As a result, when TM4SF4 was over-expressed in the adenocarcinoma cell line A549, cell infiltration was approximately 40% increased, compared with that of the control (FIG. 14, down).

Example 13

Increase of MMP (Matrix Metalloprotease) Expression by the Over-Expression of TM4SF4 in the Adenocarcinoma Cell Line A549 Among Lung Cancer Cell Lines, Confirmed by Western Blotting As shown in Examples 6-8, the low-expression of TM4SF4 in A549 cells induced the low-expressions of MMP-2, 7, and 9. To confirm the above result, Western blotting was performed in this example to investigate whether or not the over-expression of TM4SF4 could induce the over-expressions of MMP-2, 7, and 9.

The over-expression of TM4SF4 was induced in A549 cells by the same manner as described in Example 3-2. Then, whole cell lysate was obtained by the same manner as described in Example 2, followed by Western blotting to investigate the expressions of MMP-2, 7, and 9.

As a result, the over-expression of TM4SF4 in the adenocarcinoma cell line A549 increased the expressions of MMP-2, 7, and 9 (FIG. 15).

Example 14

Decrease of Cell Growth by the Treatment of Anti-TM4SF4 Antibody in the Adenocarcinoma Cell Line A549 Among Lung Cancer Cell Lines $2 \times 10^3$ A549 cells were loaded in a 60-mm cell culture dish, followed by culture. 1 μg/ml or 3 μg/ml of neutralizing anti- TM4SF4 antibody (Abcam) was treated thereto. After 5 days from the treatment, the cells were stained with 0.5% (w/v) crystal violet solution, followed by observation. The number of colonies was counted and colony survival rate was presented as % by the control.

As a result, the number of colonies was reduced the antibody dose dependently, which was consistent with the result obtained when the expression of TM4SF4 was suppressed by using siRNA (FIG. 16). The above result indicates that the membrane protein TM4SF4 plays an important role in cell growth of the adenocarcinoma cell line A549 among non-small cell lung cancer cell lines, and when the membrane protein is neutralized by the antibody cell growth is as significantly inhibited as the expression of the protein was suppressed by siRNA.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating non-small cell lung adenocarcinoma cancers or increasing radiosensitivity of non-small cell lung cancer adenocarcinoma cells, comprising administering a pharmaceutically effective dose of an inhibitor of the expression or activity of TM4SF4 (transmembrane 4 L six family member 4) to a subject having non-small cell lung adenocarcinoma, wherein the inhibitor of the expression of TM4SF4 is the antisense nucleotide or the small interfering RNA binding complementarily to TM4SF4 mRNA, or antibodies complementarily binding to TM4SF4 protein.

2. The method according to claim 1, wherein the TM4SF4 comprises the amino acid sequence set forth as SEQ ID NO: 1.

3. The method according to claim 1, wherein the radiation is gamma radiation.

4. The method according to claim 3, wherein the gene encoding TM4SF4 protein comprises the nucleic acid sequence set forth as SEQ ID NO: 2.

* * * * *